(12) United States Patent
Van Snick et al.

(10) Patent No.: US 7,157,091 B1
(45) Date of Patent: Jan. 2, 2007

(54) MAGE-A1 PEPTIDES PRESENTED BY HLA CLASS II MOLECULES

(75) Inventors: Jacques Van Snick, Brussels (BE); Bernard Lethé, Brussels (BE); Pascal Chaux, Brussels (BE); Thierry Boon-Falleur, Brussels (BE); Pierre van der Bruggen, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/336,091

(22) Filed: Jun. 18, 1999

(51) Int. Cl.
| | |
|---|---|
| C07K 19/00 | (2006.01) |
| C07K 14/435 | (2006.01) |
| C07K 11/00 | (2006.01) |
| A61K 38/04 | (2006.01) |
| A61K 38/16 | (2006.01) |

(52) U.S. Cl. .............. 424/277.1; 530/323; 530/324; 530/325; 530/326; 530/327; 530/328; 530/403; 530/806; 530/828; 530/332; 424/184.1; 424/185.1; 424/192.1; 424/193.1; 424/277.1; 514/2; 514/12; 514/13; 514/14; 514/15; 514/885

(58) Field of Classification Search .............. 530/323, 530/324, 325, 326, 327, 328, 403, 806, 828, 530/332; 424/184.1, 185.1, 192.1, 193.1, 424/277.1; 514/2, 12, 13, 14, 885, 15
See application file for complete search history.

(56) References Cited

U.S. PATENT DOCUMENTS 5,965,535 A * 10/1999 Chaux et al. .................. 514/13

6,043,347 A * 3/2000 Gelder .................. 530/388.35

FOREIGN PATENT DOCUMENTS

| WO | WO 95/04542 | 2/1995 |
|---|---|---|
| WO | WO 95/20974 | 8/1995 |
| WO | WO 97/11669 | 4/1997 |
| WO | WO 99/14326 | 3/1999 |

OTHER PUBLICATIONS

Chaux et al., *J. Exp. Med.*, 189(5):767-777 (1999).
Sanderson et al., *Proc. Natl. Acad. Sci. USA*, 92(16):7217-7221 (1995).
Spatola, *Chem.and Biochem. of Amino Acids, Peptides and Proteins*, 7:267-357 (1983).
Manici et al., *J. Exp. Med.*, 189(5):871-876 (1999).
Büeler et al., *Molecular Medicine*, 2(5): 545-555 (1996).
Topalian et al., *J. Exp. Med.*, 183(5): 1965-1971 (1996).
Topalian, S.L., *Current Opinion in Immunol.*, 6: 741-745 (1994).

* cited by examiner

*Primary Examiner*—Ronald B. Schwadron
(74) *Attorney, Agent, or Firm*—Wolf, Greenfield & Sacks, P.C.

(57) ABSTRACT

The invention provides isolated HLA DRB1*15-binding peptides consisting of the amino acid sequence set forth as SEQ ID NO:7 with 0–10 amino acids added to either or both ends of the amino acid sequence set forth as SEQ ID NO:7, and an endosomal targeting signal comprising an endosomal targeting portion of human invariant chain Ii or LAMP-1.

8 Claims, 4 Drawing Sheets

MAGE-A1 PEPTIDES PRESENTED BY HLA CLASS II MOLECULES

FIELD OF THE INVENTION

This invention relates to fragments of the tumor associated gene product MAGE-A1 which bind to and are presented to T lymphocytes by HLA class II molecules. The peptides, nucleic acid molecules which code for such peptides, as well as related antibodies and CD4$^+$ T lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response, which in part comprises mature T lymphocytes which are positive for either CD4 or CD8 cell surface proteins. T cells can recognize and interact with other cells via cell surface complexes on the other cells of peptides and molecules referred to as human leukocyte antigens ("HLAs") or major histocompatibility complexes ("MHCs"). The peptides are derived from larger molecules which are processed by the cells which also present the HLA/MHC molecule. See Male et al., *Advanced Immunology* (J.P. Lipincott Company, 1987), especially chapters 6–10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanisms described above are involved in the immune system's response to foreign materials, in autoimmune pathologies, and in responses to cellular abnormalities.

The T cell response to foreign antigens includes both cytolytic T lymphocytes and helper T lymphocytes. CD8$^+$ cytotoxic or cytolytic T cells (CTLs) are T cells which, when activated, lyse cells that present the appropriate antigen presented by HLA class I molecules. CD4$^+$ T helper cells are T cells which secrete cytokines to stimulate macrophages and antigen-presenting B cells which present the appropriate antigen by HLA class II molecules on their surface.

The mechanism by which T cells recognize alien materials also has been implicated in cancer. A number of cytolytic T lymphocyte (CTL) clones directed against autologous melanoma have been described. In some instances, the antigens recognized by these clones have been characterized. In De Plaen et al., *Immunogenetics* 40:360–369 (1994), the "MAGE" family, a family of genes encoding tumor specific antigens, is described. (See also PCT application PCT/US92/04354, published on Nov. 26, 1992.) The expression products of these genes are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics* 35: 145 (1992); van der Bruggen et al., *Science* 254: 1643 (1991), for further information on this family of genes. Also, see U.S. Pat. No. 5,342,774.

In U.S. Pat. No. 5,405,940, MAGE nonapeptides are taught which are presented by the HLA-A1 molecule. Given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,591,430, additional isolated MAGE-3 peptides are taught which are presented by the HLA-A2 molecule. Therefore, a given TRAP can yield a plurality of TRAs.

The foregoing references describe isolation and/or characterization of tumor rejection antigens which are presented by HLA class I molecules. These TRAs can induce activation and proliferation of CD8$^+$ cytotoxic T lymphocytes (CTLs) which recognize tumor cells that express the tumor associated genes (e.g. MAGE genes) which encode the TRAs.

The importance of CD4$^+$ T lymphocytes (helper T cells) in antitumor immunity has been demonstrated in animal models in which these cells not only serve cooperative and effector functions, but are also critical in maintaining immune memory (reviewed by Topalian, *Curr. Opin. Immunol.* 6:741–745, 1994). Moreover, several studies support the contention that poor tumor-specific immunity is due to inadequate activation of T helper cells.

It has recently been demonstrated that the MAGE-3 and tyrosinase genes encode peptides which are presented by HLA class II molecules to stimulate CD4$^+$ T lymphocytes (PCT/US98/18601; Topalian et al., 1994; Yee et al., *J. Immunol.* 157:4079–4086, 1996; Topalian et al., *J. Exp. Med.* 183:1965–1971, 1996).

As with many cancer associated antigens, MAGE-3 and tyrosinase are expressed in a limited percentage of tumors and in certain types of tumors. Furthermore, the MAGE-3 and tyrosinase MHC class II binding peptides are HLA-restricted peptides, recognized only by cells which express particular HLA molecules.

Therefore, there exist many patients who would not benefit from any therapy which includes helper T cell stimulation via the previously described MAGE-3 and tyrosinase peptides, either because the patient's tumor does not express MAGE-3 or tyrosinase, or because the patient does not express the appropriate HLA molecule to present the MAGE-3 or tyrosinase peptides. Accordingly, there is a need for the identification of additional tumor associated antigens which contain epitopes presented by MHC class II molecules and recognized by CD4+ lymphocytes.

SUMMARY OF THE INVENTION

It now has been discovered that the MAGE-A1 gene encodes additional tumor rejection antigens which are HLA class II binding peptides. These peptides, when presented by an antigen presenting cell having an HLA class II molecule, effectively induce the activation and proliferation of CD4$^+$ T lymphocytes.

The invention provides isolated MAGE-A1 peptides which bind HLA class II molecules, and functional variants of such peptides, the functional variants comprising one or more amino acid additions, substitutions or deletions to the MAGE-A1 peptide sequence. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits and vaccine compositions containing the foregoing molecules additionally are provided. The foregoing can be used in the diagnosis or treatment of conditions characterized by the expression of MAGE-A1. As it is known that the members of the MAGE family of polypeptides and nucleic acids including MAGE related genes share significant sequence identity and functional homology (e.g., as tumor antigens and precursors), the invention also embraces structurally-related HLA binding peptides derived from members of the MAGE and MAGE-A families other than MAGE-A1. For example, an amino acid sequence similar to the MAGE-A1 peptides disclosed herein also is found in MAGE-4 protein. Therefore, it is understood that the disclosure contained herein of MAGE-A1 HLA class II binding peptides, compositions containing such peptides, and methods of identifying and using such peptides applies also to other members of the MAGE tumor associated antigen family.

According to one aspect of the invention, an isolated MAGE-A1 HLA class II-binding peptide, comprising a fragment of the amino acid sequence of SEQ ID NO:2 which binds an HLA class II molecule, or a functional variant thereof comprising one or more amino acid additions, substitutions or deletions, is provided. The isolated peptide in one embodiment comprises the amino acid sequence of SEQ ID NO:7, or a functional variant thereof. In certain embodiments, the isolated HLA class II-binding peptide comprises an amino acid sequence selected from the group consisting of SEQ ID NO:3, SEQ ID NO:4, and SEQ ID NO:7. In preferred embodiments, the isolated peptide consists of one of the foregoing amino acid sequences. In certain embodiments, the isolated peptide comprises an endosomal targeting signal, preferably an endosomal targeting portion of human invariant chain Ii or LAMP-1. In other embodiments of the invention, the isolated HLA class II-binding peptide is non-hydrolyzable. Preferred non-hydrolyzable peptides are selected from the group consisting of peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

According to another aspect of the invention, a composition comprising an isolated MAGE-A1 HLA class I-binding peptide and an isolated MAGE-A1 HLA class II-binding peptide is provided. In certain embodiments, the MAGE-A1 HLA class I-binding peptide and the MAGE-A1 HLA class II-binding peptide are combined as a polytope polypeptide. In other embodiments the isolated MAGE-A1 HLA class II-binding peptide in the composition comprises the amino acid sequence of SEQ ID NO:7, or a functional variant thereof. Preferably, the isolated MAGE-A1 HLA class II-binding peptide in the composition comprises an amino acid sequence selected from the group consisting of SEQ ID NO:3, SEQ ID NO:4, and SEQ ID NO:7. More preferably, the MAGE-A1 HLA class II-binding peptide consists of an amino acid sequence selected from the group consisting of SEQ ID NO:3, SEQ ID NO:4, and SEQ ID NO:7. In certain embodiments of the foregoing compositions, the isolated MAGE-A1 HLA class II-binding peptide includes an endosomal targeting signal. Preferably the endosomal targeting signal includes an endosomal targeting portion of human invariant chain Ii or LAMP-1.

According to another aspect of the invention, an isolated nucleic acid encoding any of the foregoing HLA class II-binding peptides is provided. Preferably the nucleic acid comprises SEQ ID NO:12.

According to still another aspect of the invention, expression vectors are provided. The expression vectors comprise any of the foregoing isolated nucleic acids operably linked to a promoter. In preferred embodiments, the nucleic acid comprises SEQ ID NO:7. In other embodiments, the expression vector further comprise a nucleic acid which encodes an HLA-DRB 1*15 molecule.

According to yet another aspect of the invention, host cells transfected or transformed with any of the foregoing expression vectors are provided. Host cells which express an HLA-DRB 1*15 molecule, and which are transfected or transformed with any of the foregoing expression vectors are also provided.

According to another aspect of the invention, methods for enriching selectively a population of T lymphocytes with CD4$^+$ T lymphocytes specific for a MAGE-A1 HLA class II-binding peptide are provided. The methods include contacting an isolated population of T lymphocytes with an agent presenting a complex of the MAGE-A1 HLA class II-binding peptide and an HLA class II molecule in an amount sufficient to selectively enrich the isolated population of T lymphocytes with the CD4$^+$ T lymphocytes. In certain embodiments, the agent is an antigen presenting cell contacted with a MAGE-A1 protein or an HLA class II binding fragment thereof. In preferred embodiments, the HLA class II molecule is an HLA-DRB 1*15 molecule and the MAGE-A1 HLA class II-binding peptide is a peptide having the amino acid sequence of SEQ ID NO:7, or a functional variant thereof. More preferably, the MAGE-A1 HLA class II-binding peptide includes the amino acid sequence of SEQ ID NO:3, SEQ ID NO:4, or SEQ ID NO:7. In certain embodiments of the foregoing methods, the isolated MAGE-A1 protein or HLA class II binding peptide thereof includes an endosomal targeting signal. Preferably the endosomal targeting signal includes an endosomal targeting portion of human invariant chain Ii or LAMP-1.

According to a further aspect of the invention, methods for diagnosing a disorder characterized by expression of MAGE-A1 are provided. The methods include contacting a biological sample isolated from a subject with an agent that is specific for the MAGE-A1 HLA class II binding peptide, and determining the interaction between the agent and the MAGE-A1 HLA class II binding peptide as a determination of the disorder. The biological sample in some embodiments is, for example, dendritic cells loaded with a tumor cell lysate. In certain embodiments, the peptide comprises the amino acid sequence of SEQ ID NO:7, or a functional variant thereof. In preferred embodiments, the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7.

According to another aspect of the invention, methods for diagnosing a disorder characterized by expression of a MAGE-A1 HLA class II-binding peptide which forms a complex with an HLA class II molecule are provided. The methods include contacting a biological sample isolated from a subject with an agent that binds the complex; and determining binding between the complex and the agent as a determination of the disorder. In some embodiments the HLA class II molecule is an HLA-DRB1*15 molecule, and the MAGE-A1 HLA class II-binding peptide comprises the amino acid sequence of SEQ ID NO:7, or a functional variant thereof. Preferably the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7.

Methods for treating a subject having a disorder characterized by expression of MAGE-A1 are provided in another aspect of the invention. The methods include administering to the subject an amount of a MAGE-A1 HLA class II-binding peptide sufficient to ameliorate the disorder. In certain embodiments the MAGE-A1 HLA class II-binding peptide comprises the amino acid sequence of SEQ ID NO:7, or a functional variant thereof. Preferably the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7. In certain embodiments, the MAGE-A1 HLA class II binding peptide comprises an endosomal targeting signal, preferably an endosomal targeting portion of human invariant chain Ii or LAMP-1.

According to still another aspect of the invention, methods for treating a subject having a disorder characterized by expression of MAGE-A1 are provided. The methods include administering to the subject an amount of a MAGE-A1 HLA class I-binding peptide and an amount of a MAGE-A1 HLA class II-binding peptide sufficient to ameliorate the disorder. In certain embodiments, the MAGE-A1 HLA class II-binding peptide comprises the amino acid sequence of SEQ ID NO:7, or a functional variant thereof. Preferably the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7. In certain embodiments of the foregoing methods, the MAGE-A1 HLA class I-binding peptide and the MAGE-A1 HLA class II-binding peptide are combined as a polytope polypeptide. In still other embodiments, the MAGE-A1 HLA class II binding peptide comprises an endosomal targeting signal, preferably an endosomal targeting portion of human invariant chain Ii or LAMP-1.

According to yet another aspect of the invention, methods for treating a subject having a disorder characterized by expression of MAGE-A1 are provided. The methods include administering to the subject an amount of an agent which enriches selectively in the subject the presence of complexes of an HLA class II molecule and a MAGE-A1 HLA class II-binding peptide, sufficient to ameliorate the disorder. Preferably the HLA class II molecule is an HLA-DRB1*15 molecule. In certain embodiments, the MAGE-A1 HLA class II-binding peptide comprises the amino acid sequence of SEQ ID NO:7, or a functional variant thereof. Preferably the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7. In certain embodiments, the agent comprises a MAGE-A1 HLA class II binding peptide. Preferably the MAGE-A1 HLA class II binding peptide includes an endosomal targeting signal. Preferred endosomal targeting signals include endosomal targeting portions of human invariant chain Ii and LAMP-1.

Additional methods for treating a subject having a disorder characterized by expression of MAGE-A1 are provided in another aspect of the invention. The methods include administering to the subject an amount of autologous CD4+ T lymphocytes sufficient to ameliorate the disorder, wherein the CD4+ T lymphocytes are specific for complexes of an HLA class II molecule and a MAGE-A1 HLA class II-binding peptide. Preferably the HLA class II molecule is an HLA-DRB1*15 molecule. In certain embodiments, the MAGE-A1 HLA class II-binding peptide comprises the amino acid sequence of SEQ ID NO:7, or a functional variant thereof. Preferably the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7.

According to another aspect of the invention, an isolated polypeptide is provided. The isolated polypeptide binds selectively an epitope comprising a MAGE-A1 HLA class II-binding peptide, preferably SEQ ID NO:7, provided that the isolated polypeptide is not an HLA class II molecule. In certain embodiments, the isolated polypeptide is an antibody and preferably is a monoclonal antibody. In other embodiments, the isolated polypeptide is an antibody fragment selected from the group consisting of a Fab fragment, a F(ab)$_2$ fragment or a fragment including a CDR3 region selective for a MAGE-A1 HLA class II-binding peptide.

According to still another aspect of the invention, an isolated CD4+ T lymphocyte is provided. The isolated CD4+ T lymphocyte selectively binds a complex of an HLA class II molecule and a MAGE-A1 HLA class II-binding peptide. Preferably the HLA class II molecule is an HLA-DRB1*15 molecule. In some embodiments the MAGE-A1 HLA class II-binding peptide comprises the amino acid sequence of SEQ ID NO:7, or a functional variant thereof. Preferably the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7.

According to still another aspect of the invention, an isolated antigen presenting cell is provided. The isolated antigen presenting cell comprises a complex of an HLA class II molecule and a MAGE-A1 HLA class II-binding peptide. Preferably the HLA class II molecule is an HLA-DRB1*15 molecule. In certain embodiments the MAGE-A1 HLA class II-binding peptide comprises the amino acid sequence of SEQ ID NO:7, or a functional variant thereof. In preferred embodiments the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7.

Methods for identifying functional variants of a MAGE-A1 HLA class II binding peptide are provided according to another aspect of the invention. According to the methods, a MAGE-A1 HLA class II binding peptide, an HLA class II binding molecule which binds the MAGE-A1 HLA class II binding peptide, and a T cell which is stimulated by the MAGE-A1 HLA class II binding peptide presented by the HLA class II binding molecule are selected. A first amino acid residue of the MAGE-A1 HLA class II binding peptide is mutated to prepare a variant peptide. The binding of the variant peptide to HLA class II binding molecule and stimulation of the T cell are then determined, wherein binding of the variant peptide to the HLA class II binding molecule and stimulation of the T cell by the variant peptide presented by the HLA class II binding molecule indicates that the variant peptide is a functional variant. In preferred embodiments, the MAGE-A1 HLA class II binding peptide comprises the amino acid sequence of SEQ ID NO:7. More preferably, the MAGE-A1 HLA class II-binding peptide is a peptide including the amino acid sequence of any of SEQ ID NO:3, SEQ ID NO:4, or SEQ ID NO:7. More preferably, the MAGE-A1 HLA class II-binding peptide consists of the amino acid sequence of SEQ ID NO:3, SEQ ID NO:4, or SEQ ID NO:7. In certain embodiments, the methods further include the step of comparing the stimulation of the T cell by the MAGE-A1 HLA class II binding peptide and the stimulation of the T cell by the functional variant as a determination of the effectiveness of the stimulation of the T cell by the functional variant. In other embodiments, the methods include repeating the processes for identifying functional variants, using the variant peptide as a substrate. These methods include mutating a second amino acid residue of the MAGE-A1 HLA class II binding peptide (other than the mutation of the variant peptide) to prepare a second variant peptide. The binding of the second variant peptide to HLA class II binding molecule and stimulation of the T cell are then determined as for the first variant peptide. The processes can be repeated using the second variant peptide, and so on, as long as the function is tested each time. Each iteration produces variant peptides having one amino acid difference with respect to the substrate peptide. Additional methods in which more than one amino acid residue are mutated at each iteration are also included, such methods also including steps of determining function of the peptide, such as HLA class II binding molecule and/or stimulation of T cells.

The invention also provides pharmaceutical preparations containing any one or more of the medicaments described above or throughout the specification. Such pharmaceutical preparations can include pharmaceutically acceptable diluent carriers or excipients.

The use of the foregoing compositions, peptides and nucleic acids in the preparation of a medicament, particularly a medicament for treatment of cancer, also is provided.

These and other objects of the invention will be described in further detail in connection with the detailed description of the invention.

BRIEF DESCRIPTION OF THE DRAWINGS

In FIG. 4A, autologous EBV-B cells (~10,000 per microwell) were pulsed with 5 µg/ml of peptides for 2 hrs before adding ~3000 cells of clone 14. After 18 hrs of coculture, IFN-γ production in the supernatant was measured by ELISA. Peptides used were: VKVLEYVIKVSARVRF (SEQ ID NO:3); EYVIKVSARVRFFFPS (SEQ ID NO:4); ETSYVKVLEYVI (SEQ ID NO:5); VKVLEYVIKVSA (SEQ ID NO:6); EYVIKVSARVRF (SEQ ID NO:7); KVSARVRFFFPS (SEQ ID NO:8); RVRFFFPSLREA (SEQ ID NO:9); FFPSLREAALRE (SEQ ID NO:10); and LREAALREEEEGV (SEQ ID NO:11).

In FIG. 4B, autologous EBV-B cells (~10,000 per microwell) were incubated for 2 hrs with different concentrations of the peptides. Clone 14 (3000 cells) was then cocultured with peptide-pulsed cell for 20 hrs. IFN-γ production in the supernatant was measured by ELISA. Peptides used were: VKVLEYVIKVSARVRF (SEQ ID NO:3); EYVIKVSARVRFFFPS (SEQ ID NO:4); and EYVIKVSARVRF (SEQ ID NO:7).

DETAILED DESCRIPTION OF THE INVENTION

Figure 1:
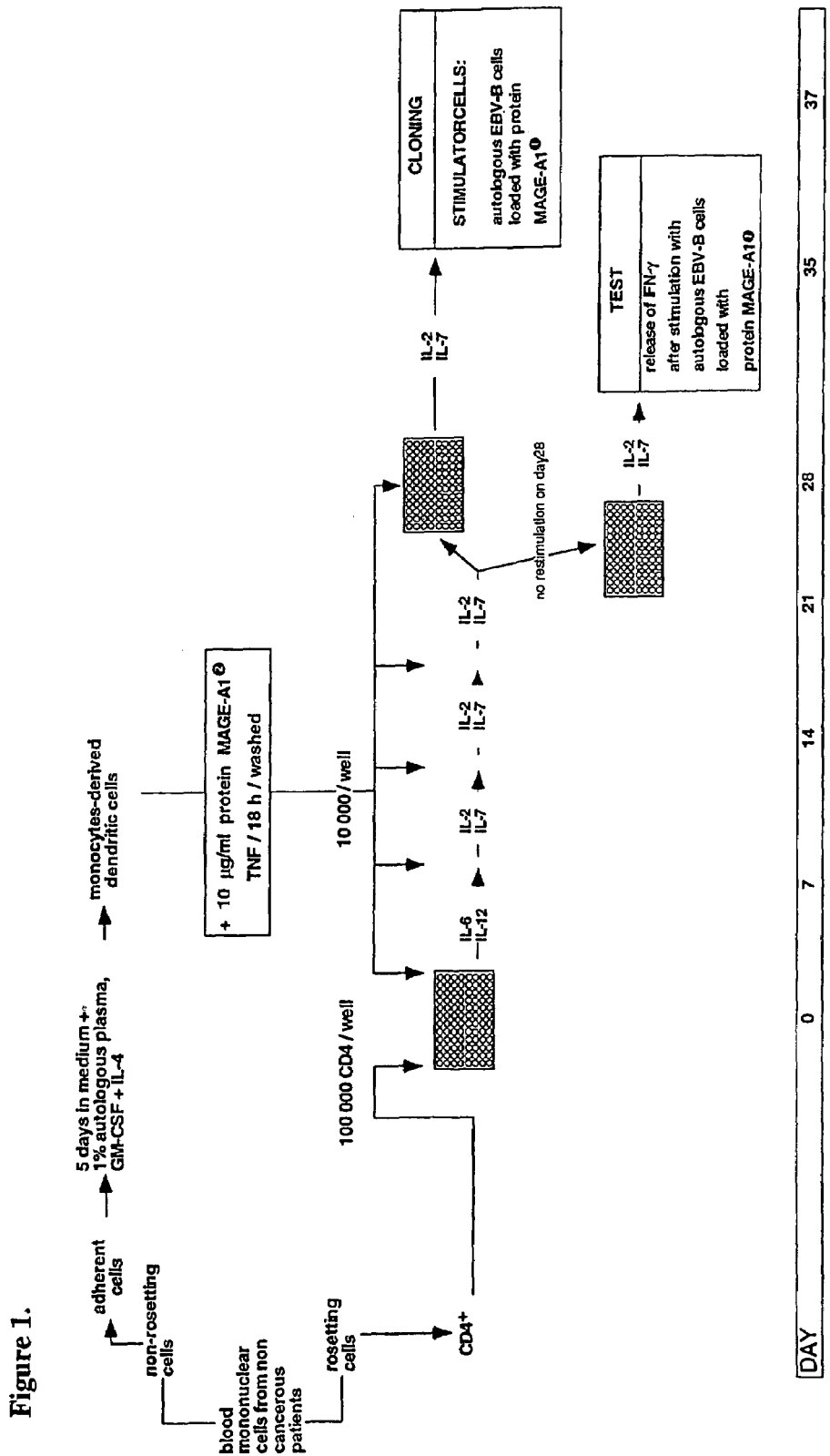
FIG. 1 is an overview of the procedure used to obtain anti-MAGE-A1 CD4+ T cell clones. The recombinant MAGE-A1® protein was produced in *E. coli*. The recombinant MAGE-A1® protein was produced in Sf9 insect cells.

The invention provides isolated MAGE-A1 peptides presented by HLA class II molecules, which peptides stimulate the proliferation and activation of CD4+ T lymphocytes. Such peptides are referred to herein as "MAGE-A1 HLA class II binding peptides", "HLA class II binding peptides" and "MHC class II binding peptides". MAGE-A1 (SEQ ID NOs: 1 and 2) is also known as MAGE-1. Hence, one aspect of the invention is an isolated peptide which includes the amino acid sequence of SEQ ID NO:7. The use of antigenic peptides presented by class II in addition to peptides presented by class I may improve the efficacy of therapeutic anti-tumor vaccination. Moreover, the knowledge of antigens presented by HLA-class II molecules will be useful for the evaluation of the immune response of cancer patients immunized with proteins or with recombinant viruses carrying entire genes coding for tumor antigens.

The examples below show the isolation of peptides which are MAGE-A1 HLA class II binding peptides. These exemplary peptides are processed translation products of the nucleic acid of SEQ ID NO:1. As such, it will be appreciated by one of ordinary skill in the art that the translation products from which a MAGE-A1 HLA class II binding peptide is processed to a final form for presentation may be of any length or sequence so long as they encompass one or more MAGE-A1 HLA class II binding peptides. As demonstrated in the examples below, peptides or proteins as small as 12 amino acids and as large as the amino acid sequence of the MAGE-A1 protein (SEQ ID NO:2) are appropriately processed, presented by HLA class II molecules and effective in stimulating CD4+ T lymphocytes. MAGE-A1 HLA class II binding peptides, such as the peptides of SEQ ID NO:3, SEQ ID NO:4 or SEQ ID NO:7 may have one, two, three, four, five, six, seven, eight, nine, ten, or more amino acids added to either or both ends. The antigenic portion of such a peptide is cleaved out under physiological conditions for presentation by HLA class II molecules. It is also well known in the art that HLA class II peptide length is variable between about 10 amino acids and about 30 amino acids (Engelhard, *Ann. Rev. Immunol.* 12:181–201, 1994). Most of the HLA class II binding peptides fall in to the length range of 12–19 amino acids. Nested sets of HLA class II binding peptides have been identified, wherein the peptides share a core sequence but have different amino acids at amino and/or carboxyl terminal ends (see, e.g., the Examples and Chicz et al., *J. Exp. Med.* 178:27–47, 1993). MAGE-A1 HLA class II binding peptides having fewer amino acids than the peptides disclosed herein. Thus additional MAGE-A1 HLA class II binding peptides, as well as MAGE family HLA class II binding peptides homologous to the MAGE-A1 HLA class II binding peptides, can be identified by one of ordinary skill in the art according to the procedures described herein.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

The procedures described in the Examples can be utilized to identify MAGE family HLA class II binding peptides. Thus, for example, one can load antigen presenting cells, such as dendritic cells of normal blood donors, with a recombinant MAGE protein (or a fragment thereof) by contacting the cells with the MAGE polypeptide or by introducing into the cells a nucleic acid molecule which directs the expression of the MAGE protein of interest. The antigen-presenting cells then can be used to induce in vitro the activation and proliferation of specific CD4 lymphocytes which recognize MAGE HLA class II binding peptides. The sequence of the peptides then can be determined as described in the Examples, e.g., by stimulating cells with peptide fragments of the MAGE protein used to stimulate the activation and proliferation of CD4 lymphocytes. Alternatively, one can load antigen presenting cells with peptides derived from a MAGE protein. For example, one can make predictions of peptide sequences derived from MAGE family proteins which are candidate HLA class II binding peptides based on the consensus amino acid sequences for binding HLA class II molecules. In this regard, see, e.g. International applications PCT/US96/03182 and PCT/US98/01373. Computer software for selecting HLA class II binding peptides is also available (TEPITOPE; Sturniolo et al., *Nature Biotechnol.* 17:555–561, 1999; Manici et al., *J. Exp. Med.* 189:871–876, 1999). Peptides which are thus selected can be used in the assays described herein for inducing specific CD4 lymphocytes and identification of peptides. Additional methods of selecting and testing peptides for HLA class II binding are well known in the art.

As noted above, the invention embraces functional variants of MAGE-A1 HLA class II binding peptides. As used herein, a "functional variant" or "variant" of a HLA class II binding peptide is a peptide which contains one or more modifications to the primary amino acid sequence of a HLA class II binding peptide and retains the HLA class II and T cell receptor binding properties disclosed herein. Modifications which create a MAGE-A1 HLA class II binding peptide functional variant can be made for example 1) to enhance a property of a MAGE-A1 HLA class II binding peptide, such as peptide stability in an expression system or the stability of protein—protein binding such as HLA-peptide binding; 2) to provide a novel activity or property to a MAGE-A1 HLA class II binding peptide, such as addition of an antigenic epitope or addition of a detectable moiety; or 3) to provide a different amino acid sequence that produces the same or similar T cell stimulatory properties. Modifications to MAGE-A1 (as well as MAGE family) HLA class II binding peptides can be made to nucleic acids which encode the peptide, and can include deletions, point mutations, truncations, amino acid substitutions and additions of amino acids. Alternatively, modifications can be made directly to the polypeptide, such as by cleavage, addition of a linker molecule, addition of a detectable moiety (such as biotin), addition of a fatty acid, substitution of one amino acid for another and the like. Variants also can be selected from libraries of peptides, which can be random peptides or peptides based on the sequence of the MAGE peptides including substitutions at one or more positions. For example, a peptide library can be used in competition assays with complexes of MAGE peptides bound to HLA class II molecules (e.g. dendritic cells loaded with a MAGE-A1 HLA class II binding peptide). Peptides which compete for binding of the MAGE peptide to the HLA class II molecule can be sequenced and used in other assays (e.g. CD4 lymphocyte proliferation) to determine suitability as MAGE peptide functional variants. Other functional variants can be peptidomimetic compounds. Peptidomimetics can be prepared and tested for HLA class II binding (see Falcioni et al., *Nature Biotechnol.* 17:562–567, 1999) and then tested for stimulation of $CD4^+$ T cells.

Modifications also embrace fusion proteins comprising all or part of a MAGE HLA class II binding peptide amino acid sequence, such as the invariant chain-MAGE-A1 fusion proteins. The invention thus embraces fusion proteins comprising MAGE-A1 HLA class II binding peptides and endosomal targeting signals such as the human invariant chain (Ii) or LAMP-1. Fusion of an endosomal targeting portion of human invariant chain to MAGE-A1 results in efficient targeting of MAGE-A1 to the HLA class II peptide presentation pathway. An "endosomal targeting portion" of the human invariant chain or other targeting polypeptide is that portion of the molecule which, when fused or conjugated to a second polypeptide, increases endosomal localization of the second polypeptide. Thus endosomal targeting portions can include the entire sequence or only a small portion of a targeting polypeptide such as human invariant chain Ii. One of ordinary skill in the art can readily determine an endosomal targeting portion of a targeting molecule. Additional endosomal targeting signals can be identified by one of ordinary skill in the art, fused to MAGE-A1 or a MAGE-A1 HLA class II binding portion thereof, and tested for targeting to the HLA class II peptide presentation pathway using no more than routine experimentation. For an example of a fusion polypeptide including an endosomal targeting signal portion and a HLA class II binding peptide portion, see published PCT application PCT/US98/18601.

The amino acid sequence of MAGE HLA class II binding peptides may be of natural or non-natural origin, that is, they may comprise a natural MAGE HLA class II binding peptide molecule or may comprise a modified sequence as long as the amino acid sequence retains the ability to stimulate helper T cells when presented and retains the property of binding to an HLA class II molecule such as an HLA-DRB1*15 molecule. For example, MAGE-A1 HLA class II binding peptides in this context may be fusion proteins including a MAGE-A1 HLA class II binding peptide and unrelated amino acid sequences, synthetic peptides of amino acid sequences shown in SEQ ID NOs:3, 4 and 7, labeled peptides, peptides isolated from patients with a MAGE expressing cancer, peptides isolated from cultured cells which express MAGE-A1, peptides coupled to nonpeptide molecules (for example in certain drug delivery systems) and other molecules which include the amino acid sequence of SEQ ID NO:3, SEQ ID NO:4 or SEQ ID NO:7.

Preferably, MAGE HLA class II binding peptides are non-hydrolyzable. To provide such peptides, one may select MAGE HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing $CD4^+$ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a MAGE-A1 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[$CH_2NH$]-reduced amide peptide bonds, -psi[$COCH_2$]-ketomethylene peptide bonds, -psi[$CH(CN)NH$]-(cyanomethylene)amino peptide bonds, -psi[$CH_2CH(OH)$]-hydroxyethylene peptide bonds, -psi[$CH_2O$]-peptide bonds, and -psi[$CH_2S$]-thiomethylene peptide bonds.

Nonpeptide analogs of peptides, e.g., those which provide a stabilized structure or lessened biodegradation, are also contemplated. Peptide mimetic analogs can be prepared based on a selected MAGE-A1 HLA class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., *Regul. Pept.* 57:359–370 (1995). Peptide as used herein embraces all of the foregoing.

If a variant involves a change to an amino acid of SEQ ID NO:3, SEQ ID NO:4, or SEQ ID NO:7, functional variants of the MAGE-A1 HLA class II binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the MAGE-A1 HLA class II binding peptides are provided in a published PCT application of Strominger and Wucherpfennig (PCT/US96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Sequence motifs for MAGE-A1 HLA class II binding peptide functional variants can be developed by analysis of the binding domains or binding pockets of major histocompatibility complex HLA-DR proteins and/or the T cell receptor ("TCR") contact points of the MAGE-A1 HLA class II binding peptides disclosed herein. By providing a detailed structural analysis of the residues involved in forming the HLA class II binding pockets, one is enabled to make predictions of sequence motifs for binding of MAGE peptides to any of the HLA class II proteins.

Using these sequence motifs as search, evaluation, or design criteria, one is enabled to identify classes of peptides (e.g. MAGE HLA class II binding peptides, particularly the MAGE-A1 peptides disclosed herein, and functional variants thereof) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. By keeping the residues which are likely to bind in the HLA class II and/or TCR binding pockets constant or permitting only specified substitutions, functional variants of MAGE HLA class II binding peptides can be prepared which retain binding to HLA class II and T cell receptor.

Thus, methods for identifying additional MAGE family HLA class II peptides, in particular MAGE-A1 HLA class II binding peptides, and functional variants thereof, are provided. In general, any MAGE protein can be subjected to the analysis noted above, peptide sequences selected and the tested as described herein. With respect to MAGE-A1, for example, the methods include selecting a MAGE-A1 HLA class II binding peptide, an HLA class II binding molecule which binds the MAGE-A1 HLA class II binding peptide, and a T cell which is stimulated by the MAGE-A1 HLA class II binding peptide presented by the HLA class II binding molecule. In preferred embodiments, the MAGE-A1 HLA class II binding peptide comprises the amino acid sequence of SEQ ID NO:7. More preferably, the peptide consists of the amino acid sequence of SEQ ID NO:3, SEQ ID NO:4 or SEQ ID NO:7. A first amino acid residue of the MAGE-A1 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecule and stimulation of the T cell are then determined according to standard procedures. For example, as exemplified below, the variant peptide can be contacted with an antigen presenting cell which contains the HLA class II molecule which binds the MAGE-A1 peptide to form a complex of the variant peptide and antigen presenting cell. This complex can then be contacted with a T cell which recognizes the MAGE-A1 HLA class II binding peptide presented by the HLA class II binding molecule. T cells can be obtained from a patient having a condition characterized by expression of MAGE-A1. Recognition of variant peptides by the T cells can be determined by measuring an indicator of T cell stimulation such as TNF or IFNγ production. Similar procedures can be carried out for identification and characterization of other MAGE family HLA class II binding peptides.

Binding of a variant peptide to the HLA class II binding molecule and stimulation of the T cell by the variant peptide presented by the HLA class II binding molecule indicates that the variant peptide is a functional variant. The methods also can include the step of comparing the stimulation of the T cell by the MAGE-A1 HLA class II binding peptide and the stimulation of the T cell by the functional variant as a determination of the effectiveness of the stimulation of the T cell by the functional variant. By comparing the functional variant with the MAGE-A1 HLA class II binding peptide, peptides with increased T cell stimulatory properties can be prepared.

Variants of the MAGE-A1 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a MAGE HLA class II binding peptides or variant thereof and other nucleic acid sequences which hybridize to a nucleic acid molecule consisting of the above described nucleotide sequences, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15M Sodium Chloride/0.15M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1×SSC/0.1×SDS at 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the MAGE HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 90% amino acid identity and/or at least 75% nucleotide identity to the amino acid sequence of a MAGE-A1 HLA class II binding peptide (such as SEQ ID NO:3, SEQ ID NO:4 or SEQ ID NO:7 or nucleic acids which encode such a peptide, respectively. In some instances homologs and alleles will share at least 95% nucleotide identity and/or at least 90% amino acid identity and in still other instances will share at least 99% nucleotide identity and/or at least 95% amino acid identity. Complements of the foregoing nucleic acids also are embraced by the invention.

In screening for nucleic acids which encode a MAGE HLA class II binding peptide, a nucleic acid hybridization such as a Southern blot or a Northern blot may be performed using the foregoing conditions, together with a $^{32}p$ probe. After washing the membrane to which DNA encoding a MAGE HLA class II binding peptide was finally transferred, the membrane can be placed against X-ray film to detect the radioactive signal.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

The invention also includes the use of nucleic acid sequences which include alternative codons that encode the same amino acid residues of the MAGE HLA class II binding peptides. For example, as disclosed herein, the peptide EYVIKVSARVRF (SEQ ID NO:7) is a MAGE-A1 HLA class II binding peptide. The serine residue (amino acid No. 7 of SEQ ID NO:7) can be encoded by the codons UCU, UCC, UCA, UCG, AGU and AGC. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the MAGE-A1 HLA class II binding peptide of SEQ ID NO:7 include: CGA, CGC, CGG, CGT, AGA and AGG (arginine codons); AAA and AAG (lysine codons); GUA, GUC, GUG and GUU (valine codons); GAA and GAG (glutamine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native MAGE HLA class II binding peptide encoding nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, enzymatic activity, receptor binding, formation of complexes by binding of peptides by MHC class I or class II molecules, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DRB1*15 molecules present a MAGE-A1 HLA class II binding peptide, the expression vector may also include a nucleic acid sequence coding for an HLA-DRB 1*15 molecule. (For other MAGE HLA class II binding peptides, different HLA molecules can be used.) In a situation where the vector contains both coding sequences, it can be used to transfect a cell which does not normally express either one. The MAGE-A1 HLA class II binding peptide coding sequence may be used alone, when, e.g. the host cell already expresses an HLA-DRB1*15 molecule. Of course, there is no limit on the particular host cell which can be used as the vectors which contain the two coding sequences may be used in host cells which do not express HLA-DRB1*15 molecules if desired, and the nucleic acid coding for the MAGE-A1 HLA class II binding peptide can be used in antigen presenting cells which express an HLA-DRB1*15 molecule. As used herein, "an HLA-DRB1*15 molecule" includes the subtypes DRB1*15011, DRB1*15012, DRB1*15021, DRB1*15022, DRB1*15023, DRB1*1503, DRB1*1504, DRB1*1505, DRB1*1506, DRB1*1507, and DRB1*1508. An HLA-DRB1*15 molecule also includes the subtypes which can be found in Bodmer et al., *Tissue Antigens* 49:297, 1996 and at the IMGT/HLA Database website at http://mercury.ebi.ac.uk/imgt/hla/.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target a MAGE family polypeptide, e.g. MAGE-A1, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore it is preferable that the MAGE-A1 HLA class II binding peptides and precursors thereof (e.g. the MAGE-A1 protein) are targeted to the endosome, thereby enhancing MAGE-A1 HLA class II binding peptide binding to HLA class II molecules. Targeting signals for directing molecules to endosomes are known in the art and these signals conveniently can be incorporated in expression vectors such that fusion proteins which contain the endosomal targeting signal are produced. Sanderson et al. (*Proc. Nat'l. Acad. Sci. USA* 92:7217–7221, 1995), Wu et al. (*Proc. Nat'l. Acad. Sci. USA* 92:11671–11675, 1995) and Thomson et al (*J. Virol.* 72:2246–2252, 1998) describe endosomal targeting signals (including invariant chain Ii and lysosomal-associated membrane protein LAMP-1) and their use in directing antigens to endosomal and/or lysosomal cellular compartments.

Endosomal targeting signals such as invariant chain also can be conjugated to MAGE-A1 protein or peptides by non-peptide bonds (i.e. not fusion proteins) to prepare a conjugate capable of specifically targeting MAGE-A1. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulflhydryls, carboxyls, carbonyls and carbohydrates. One of ordinary skill in the art will be able to ascertain without undue experimentation the preferred molecule for linking the endosomal targeting moiety and MAGE-A1 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a MAGE-A1 HLA class II binding peptide. That heterologous DNA (RNA) is placed under operable control of transcriptional elements to permit the expression of the heterologous DNA in the host cell. As described herein, such expression constructs optionally also contain nucleotide sequences which encode endosomal targeting signals, preferably human invariant chain or a targeting fragment thereof.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996).

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for MAGE-A1 HLA class II binding peptides but are equally applicable to use of other structurally or functionally related MAGE family HLA class II binding peptides. First, the invention permits the artisan to diagnose a disorder characterized by expression of a MAGE-A1 HLA class II binding peptide. These methods involve determining expression of a MAGE-A1 HLA class II binding peptide, or a complex of a MAGE-A1 HLA class II binding peptide and an HLA class II molecule in a biological sample. The expression of a peptide or complex of peptide and HLA class II molecule can be determined by assaying with a binding partner for the peptide or complex, such as an antibody.

The invention also permits the artisan to treat a subject having a disorder characterized by expression of a MAGE-A1 HLA class II binding peptide. Treatments include administering an agent which enriches in the subject a complex of a MAGE-A1 HLA class II binding peptide and an HLA class II molecule, and administering CD4+ T lymphocytes which are specific for such complexes. Agents useful in the foregoing treatments include MAGE-A1 HLA class II binding peptides and functional variants thereof, endosome-targeted fusion proteins which include such MAGE-A1 peptides, nucleic acids which express such proteins and peptides (including viruses which contain the nucleic acids), complexes of such peptides and HLA class II binding molecules (e.g. HLA-DRB1*15), antigen presenting cells bearing complexes of a MAGE-A1 HLA class II binding peptide and an HLA class II binding molecule, and the like. The invention also permits an artisan to selectively enrich a population of T lymphocytes for CD4+ T lymphocytes specific for a MAGE-A1 HLA class II binding peptide.

The isolation of the MAGE-A1 HLA class II binding peptides also makes it possible to isolate nucleic acids which encode the MAGE-A1 HLA class II binding peptides. Nucleic acids can be used to produce in vitro or in prokaryotic or eukaryotic host cells the MAGE-A1 HLA class II binding peptides. A variety of methodologies well-known to the skilled practitioner can be utilized to obtain isolated MAGE-A1 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the MAGE-A1 HLA class II binding peptide of the invention may also be synthesized in vitro. Those skilled in the art also can readily follow known methods for isolating peptides in order to obtain isolated MAGE-A1 HLA class II binding peptides. These include, but are not limited to, immunochromotography, HPLC, size-exclusion chromatography, ion-exchange chromatography and immune-affinity chromatography.

These isolated MAGE-A1 HLA class II binding peptides, proteins which include such peptides, or complexes of the peptides and HLA class II molecules, such as an HLA-DRB1*15 molecule, may be combined with materials such as adjuvants to produce vaccines useful in treating disorders characterized by expression of the MAGE-A1 HLA class II binding peptide. In addition, vaccines can be prepared from cells which present the MAGE-A1 HLA class II binding peptide/HLA complexes on their surface, such as dendritic cells, B cells, non-proliferative transfectants, etcetera. In all cases where cells are used as a vaccine, these can be cells transfected with coding sequences for one or both of the components necessary to stimulate CD4+ lymphocytes, or be cells which already express both molecules without the need for transfection. For example, autologous antigen presenting cells can be isolated from a patient and treated to obtain cells which present MAGE-A1 epitopes in association of HLA class I and HLA class II molecules. These cells would be capable of stimulating both CD4+ and CD8+ cell responses. Such antigen presenting cells can be obtained, for example, by infecting dendritic cells with recombinant viruses encoding an Ii.MAGE-A1 fusion protein. Dendritic cells also can be loaded with HLA class I and HLA class II epitopes.

Vaccines also encompass naked DNA or RNA, encoding a MAGE-A1 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259: 1745–1748, 1993). Vaccines also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a given antigen can be detected by direct labeling of T cell receptors with soluble fluorogenic MHC molecule tetramers which present the antigenic peptide (Altman et al., *Science* 274:94–96, 1996; Dunbar et al., *Curr. Biol.* 8:413–416, 1998). Briefly, soluble MHC class I molecules are folded in vitro in the presence of β2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675–682, 1998). Multimeric soluble MHC class II molecules were complexed with a covalently attached peptide. The class II tetramers were shown to bind with appropriated specificity and affinity to specific T cells. Thus tetramers can be used to monitor both CD4+ and CD8+ cell responses to vaccination protocols.

The MAGE-A1 HLA class II binding peptide, as well as complexes of MAGE-A1 HLA class II binding peptide and HLA molecule, also may be used to produce antibodies, using standard techniques well known to the art. Standard reference works setting forth the general principles of antibody production include Catty, D., *Antibodies, A Practical Approach*, Vol. 1, IRL Press, Washington D.C. (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the peptide/HLA complexes described herein.

When "disorder" or "condition" is used herein, it refers to any pathological condition where the MAGE-A1 HLA class II binding peptide is expressed. Such disorders include cancers, such as melanomas, squamous cell carcinomas of the head, neck, lung or esophagus, colorectal carcinomas, osteosarcomas, neuroblastomas, non-squamous cell carcinomas of the head or neck, ovarian tumors, lymphocytic leukemias, bladder carcinomas, prostate carcinomas, mammary carcinomas and gastric carcinomas.

Some therapeutic approaches based upon the disclosure are premised on inducing a response by a subject's immune system to MAGE HLA class II binding peptide presenting cells. One such approach is the administration of autologous $CD4^+$ T cells specific to the complex of MAGE-A1 HLA class II binding peptide and an HLA class II molecule to a subject with abnormal cells of the phenotype at issue. It is within the skill of the artisan to develop such $CD4^+$ T cells in vitro. Generally, a sample of cells taken from a subject, such as blood cells, are contacted with a cell presenting the complex and capable of provoking $CD4^+$ T lymphocytes to proliferate. The target cell can be an antigen presenting cell bearing HLA class II molecules, such as dendritic cells or B cells. A target cell can also be a transfectant such as a COS cell if the sample of cells is first sorted to isolate the $CD4^+$ T lymphocyte population. Tetramer technology, described above, may be used for sorting. These transfectants present the desired complex of their surface and, when combined with a $CD4^+$ T lymphocyte of interest, stimulate its proliferation. COS cells are widely available, as are other suitable host cells. Specific production of $CD4^+$ T lymphocytes is described below. The clonally expanded autologous $CD4^+$ T lymphocytes then are administered to the subject. The $CD4^+$ T lymphocytes then stimulate the subject's immune response, thereby achieving the desired therapeutic goal.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a MAGE-A1 sequence.

The foregoing therapy is not the only form of therapy that is available in accordance with the invention. $CD4^+$ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (Proc. Natl. Acad. Sci. USA 88: 110–114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a MAGE-A1 HLA class II binding peptide may be operably linked to promoter and enhancer sequences which direct expression of the MAGE-A1 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding MAGE-A1 HLA class II binding peptides. Nucleic acids encoding a MAGE-A1 HLA class II binding peptide also may be inserted into a retroviral genome, thereby facilitating integration of the nucleic acid into the genome of the target tissue or cell type. In these systems, the gene of interest is carried by a microorganism, e.g., a Vaccinia virus, poxviruses in general, adenovirus, herpes simplex virus, retrovirus or the bacteria BCG, and the materials de facto "infect" host cells. The cells which result present the complex of interest, and are recognized by autologous $CD4^+$ T cells, which then proliferate.

A similar effect can be achieved by combining a MAGE HLA class II binding peptide with an adjuvant to facilitate incorporation into HLA class II presenting cells in vivo. If larger than the HLA class II binding portion, the MAGE-A1 HLA class II binding peptide can be processed if necessary to yield the peptide partner of the HLA molecule while the TRA is presented without the need for further processing. Generally, subjects can receive an intradermal injection of an effective amount of the MAGE-A1 HLA class II binding peptide. Initial doses can be followed by booster doses, following immunization protocols standard in the art.

A preferred method for facilitating incorporation of MAGE-A1 HLA class II binding peptides into HLA class II presenting cells is by expressing in the presenting cells a polypeptide which includes an endosomal targeting signal fused to a MAGE-A1 polypeptide which includes the class II binding peptide. Particularly preferred are MAGE-A1 fusion proteins which contain human invariant chain Ii.

Any of the foregoing compositions or protocols can include also MAGE HLA class I binding peptides for induction of a cytolytic T lymphocyte response. For example, as demonstrated below, the MAGE-A1 protein can be processed in a cell to produce both HLA class I and HLA class II responses. Several such peptides have been described in U.S. Pat. Nos. 5,405,940 and 5,558,995. By administering MAGE-A1 peptides which bind HLA class I and class II molecules (or nucleic acid encoding such peptides), an improved immune response may be provided by inducing both T helper cells and T killer cells.

In addition, non-MAGE-A1 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in the foregoing MAGE-A1 compositions and vaccines.

Especially preferred are nucleic acids encoding a series of epitopes, known as "polytopes". The epitopes can be arranged in sequential or overlapping fashion (see, e.g., Thomson et al., Proc. Natl. Acad. Sci. USA 92:5845–5849, 1995; Gilbert et al., Nature Biotechnol. 15:1280–1284, 1997), with or without the natural flanking sequences, and can be separated by unrelated linker sequences if desired. The polytope is processed to generated individual epitopes which are recognized by the immune system for generation of immune responses.

Thus, for example, MAGE-A1 HLA class II binding peptides can be combined with peptides from other tumor rejection antigens (e.g. by preparation of hybrid nucleic acids or polypeptides) and with MAGE-A1 HLA class I binding peptides (some of which are listed below) to form "polytopes". Exemplary tumor associated peptide antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2 (HOM-MEL-40), SSX-1, SSX-4, SSX-5, SCP-1 and CT-7. For example, antigenic peptides characteristic of tumors include those listed in Table 1 below.

TABLE 2

Exemplary Antigens

| Gene | HLA | Peptide | Position | SEQ ID NO |
|---|---|---|---|---|
| MAGE-A1 | A1 | EADPTGHSY | 161–169 | 15 |
|  | A3 | SLFRAVITK | 96–104 | 16 |
|  | A24 | NYKHCFPEI | 135–143 | 17 |
|  | A28 | EVYDGREHSA | 222–231 | 18 |
|  | B37 | REPVTKAEML | 120–129 | 19 |
|  | B53 | DPARYEFLW | 258–266 | 20 |
|  | Cw2 | SAFPTTINF | 62–70 | 21 |
|  | Cw3, Cw16 | SAYGEPRKL | 230–238 | 22 |
|  | DR13 | LLKYRAREPVTKAE | 114–127 | 23 |
| MAGE-A2 | A2 | YLQLVFGIEV | 157–166 | 24 |
|  | B37 | REPVTKAEML | 127–136 | 19 |
|  | DR13 | LLKYRAREPVTKAE | 121–134 | 23 |
| MAGE-A3 | A1 | EVDPIGHLY | 168–176 | 25 |
|  | A2 | FLWGPRALV | 271–279 | 26 |
|  | A2 | KVAELVHFL | 112–120 | 27 |
|  | A24 | IMPKAGLLI | 195–203 | 28 |
|  | A24 | TFPDLESEF | 97–105 | 29 |
|  | B44 | MEVDPIGHLY | 167–176 | 30 |
|  | DR13 | AELVHFLLLKYRAR | 114–127 | 31 |
|  | DR13 | LLKYRAREPVTKAE | 121–134 | 23 |
|  | DR11 | TSYVKVLHHMVKISG | 281–295 | 32 |
| MAGE-A4 | A2 | GVYDGREHTV | 230–239 | 33 |
| MAGE-A6 | A34 | MVKISGGPR | 290–298 | 34 |
|  | B37 | REPVTKAEML | 127–136 | 19 |
|  | DR13 | LLKYRAREPVTKAE | 121–134 | 23 |
|  | Cw16 | KISGGPRISYPL | 292–303 | 35 |
| MAGE-A10 | A2 | GLYDGMEHL | 254–262 | 36 |
| MAGE-A12 | A2 | FLWGPRALV | 271–279 | 26 |
| BAGE | Cw16 | AARAVFLAL | 2–10 | 37 |
| GAGE-1, 2, 8 | Cw6 | YRPRPRRY | 9–16 | 38 |
| GAGE-3 to 7 | A29 | YYWPRPRRY | 10–18 | 39 |
| NY-ESO-1 | A2 | QLSLLMWITQC | 155–165 | 40 |
|  | A2 | SLLMWITQCFL | 157–167 | 41 |
|  | A2 | SLLMWITQC | 157–165 | 42 |
|  | A2 | QLSLLMWIT | 155–163 | 43 |
|  | A31 | ASGPGGGAPR | 53–62 | 44 |
|  | A31 | LAAQERRVPR | alt.ORF | 45 |
| GnTV | A2 | VLPDVFIRC(V) | 2–10/11 | 46, 47 |
|  | A2 | VLPDVFIRC | 38–64[1] | 46 |
| TRP2-INT2 | A68011 | EVISCKLIKR | intron 2 | 48 |
| RAGE | B7 | SPSSNRIRNT | 11–20 | 49 |
| MUM-1 | B44 | EEKLIVVLF | exon 2/intron | 50 |
|  | B44 | EEKLSVVLF (wild type) | exon 2/intron | 51 |
| CDK4 | A2 | ACDPHSGHFV | 23–32 | 52 |
|  | A2 | ARDPHSGHFV (wild type) | 23–32 | 53 |
| β-catenin | A24 | SYLDSGIHF | 29–37 | 54 |
|  | A24 | SYLDSGIHS (wild type) | 29–37 | 55 |
| Tyrosinase | A2 | MLLAVLYCL | 1–9 | 56 |
|  | A2 | YMNGTMSQV | 369–377 | 57 |
|  | A2 | YMDGTMSQV | 369–377 | 58 |
|  | A24 | AFLPWHRLF | 206–214 | 59 |
|  | B44 | SEIWRDIDF | 192–200 | 60 |
|  | B44 | YEIWRDIDF | 192–200 | 61 |
|  | DR4 | QNILLSNAPLGPQFP | 56–70 | 62 |
|  | DR4 | DYSYLQDSDPDSFQD | 448–462 | 63 |
| Melan-A[MART-1] | A2 | (E)AAGIGILTV | 26/27–35 | 64, 65 |
|  | A2 | ILTVILGVL | 32–40 | 66 |
| gp100[Pmel117] | A2 | KTWGQYWQV | 154–162 | 67 |
|  | A2 | ITDQVPFSV | 209–217 | 68 |
|  | A2 | YLEPGPVTA | 280–288 | 69 |
|  | A2 | LLDGTATLRL | 457–466 | 70 |
|  | A2 | VLYRYGSFSV | 476–485 | 71 |
| PRAME | A24 | LYVDSLFFL | 301–309 | 72 |

[1] Aberrant transcript of N-acetyl galactosaminyl transferase V (GnTV) that is found only in melanomas.

Other examples of HLA class I and HLA class II binding peptides will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more MAGE-A1 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g.

concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13): 5845–5849, 1995; Gilbert et al., *Nature Biotechnol.* 15(12): 1280–1284, 1997; Thomson et al., *J. Immunol.* 157(2): 822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, DQS21, described in PCT application WO96/33739 (SmithKline Beecham), vitamin E and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (*Science* 268: 1432–1434, 1995), GM-CSF and IL-18.

There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284–6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). Tumor cell transfection with B7 has been discussed in relation to in vitro CTL expansion for adoptive transfer immunotherapy by Wang et al. (*J. Immunother.* 19:1–8, 1996). Other delivery mechanisms for the B7 molecule would include nucleic acid (naked DNA) immunization (Kim et al., *Nature Biotechnol.* 15:7:641–646, 1997) and recombinant viruses such as adeno and pox (Wendtner et al., *Gene Ther.* 4:726–735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263–266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.,* 158:637–642, 1997; Fenton et al., *J. Immunother.,* 21:95–108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., Nature 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the MAGE-A1 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Example 1

Identification of a MAGE-A1 Epitope Presented by HLA class II Molecules to CD4+ T Lymphocytes Monocyte-derived dendritic cells were loaded with a MAGE-A1 recombinant protein and used to stimulate autologous CD4+ T cells. A CD4+ T cell clone was isolated that recognized peptide MAGE-A1$_{281-292}$ (SEQ ID NO:7) presented by HLA-DRB1*15 molecules, which are expressed in 17% of Caucasians.

I. Cell Lines, Cytokines

EBV-transformed B (EBV-B) cell lines were cultured in Iscove's modified Dulbecco medium (IMDM) (Gibco BRL, Gaithersburg, Md., USA) supplemented with 10% foetal calf serum (FCS) (Gibco BRL), 0.24 mM L-asparagine, 0.55 mM L-arginine, 1.5 mM L-glutamine (AAG), 100 U/ml penicillin and 100 µg/ml streptomycin. Human recombinant IL-2 was purchased from Eurocetus (Amsterdam, Netherlands), IL-7 from Genzyme (Cambridge, Mass., USA), GM-CSF from Schering Plough (Brinny, Ireland) and TNF-α from R&D Systems (Abingdon, UK). Human recombinant IL-4, IL-6 and IL-12 were produced in the laboratory using standard recombinant procedures.

II. Production of Two Recombinant MAGE-A1 Proteins

A-Production of the LipoD-MAGE-A1-His Protein in *E. coli*

The recombinant LipoD-MAGE-A1-His protein was produced by the SmithKline Beecham Corporation Pharmaceutical Company (Rixensart, Belgium). It contains one third of the sequence of the *Haemophilus influenzae* Lipo D protein at its N-terminal extremity and a polyhistidine marker of 7 residues (SEQ ID NO:73) at its C-terminal end, with MAGE-A1 protein (SEQ ID NO:2) between the Lipo D and His termini. This recombinant protein was produced in *E. coli* and is hereafter referred to as protein MAGE-A1*.

B-Production of the His-MAGE-A1 Protein in Sf9 Insect Cells

Another recombinant MAGE-A1 protein was produced in the laboratory in *Spodoptera frugiperda* (Sf9) insect cells using a baculovirus expression system (PharMingen, San Diego, Calif., USA). The coding sequence of MAGE-A1 (nucleotides 139–1068 of SEQ ID NO:1) was cloned in a baculovirus transfer vector (pAcGP67-A; PharMingen) downstream to the signal sequence of the gp67 surface protein of *Autographa californica* nuclear polyhedrosis virus (AcNPV), a strain of baculovirus. For easier purification, a sequence encoding a histidine tail was added at the C-terminus of the sequence of MAGE-A1. This construct allowed for secretion by the insect cells of a MAGE-A1 protein, hereafter referred to as MAGE-A1®. DNA of the recombinant plasmid was co-transfected with DNA of lethally mutated AcNPV into Sf9 insect cells. Co-transfection allows recombination between homologous regions of the plasmid and the virus, transferring the foreign gene from the vector to the AcNPV DNA. Purification of the protein contained in the supernatant of Sf9 insect cell cultures involved different steps, as described below, for different batches.

Batch no. 1 of MAGE-A1® was purified by sequential steps of filtration, anion exchange resin (DEAE-sephadex), HighTrap chelating column saturated with NiCl$_2$, affinity chromatography with an immobilized anti-MAGE-A1 monoclonal antibody (MAb 11B2), concentration and dialysis.

Batch no. 2 of MAGE-A1® was purified by sequential steps of filtration, anion exchange resin DEAE-sephadex, HighTrap chelating column saturated with NiCl$_2$, reverse phase HPLC, and concentration.

III. Processing of Human Blood

Peripheral blood was obtained from hemochromatosis patients as standard buffy coat preparations. Peripheral blood mononuclear cells (PBMC) were isolated by centrifugation on Lymphoprep (Nycomed Pharma, Oslo, Norway). In order to minimize contamination of PBMC by platelets, the preparation was first centrifuged for 20 min at 1,000 rpm at room temperature. After removal of the top 20–25 ml, containing most of the platelets, the tubes were centrifuged for 20 min at 1,500 rpm at room temperature. The interphase containing the PBMC was harvested and then washed 3 times (or more) in cold phosphate buffer solution with 2 mM EDTA in order to eliminate the remaining platelets. To generate autologous dendritic cells, PBMC were depleted from T lymphocytes by rosetting with sheep erythrocytes (BioMérieux, Marcy l'Etoile, France) treated with 2-aminoethylisothiouronium (Sigma). The lymphocyte-depleted PBMC were left to adhere for 2 h at 37° C. in culture flasks (Falcon) at a density of $2 \times 10^6$ cells/ml in RPMI 1640 medium supplemented with AAG and 1% autologous plasma (hereafter referred to as complete RPMI medium). Non-adherent cells were discarded and adherent cells were cultured in the presence of IL-4 (100 U/ml) and GM-CSF (100 ng/ml) in complete RPMI medium. Cultures were fed on day 2 and 4 by replacing half of the medium with fresh medium plus IL-4 (100 U/ml) and GM-CSF (100 ng/ml). On day 5, the non-adherent cell population was used as a source of enriched dendritic cells.

Rosetted T cells were treated with $NH_4Cl$ (160 mM) to lyse the sheep erythrocytes, and washed. CD4$^+$ T lymphocytes were isolated from rosetted T cells by negative selection using an anti-CD8 monoclonal antibody coupled to magnetic microbeads (Miltenyi Biotech, Germany) and by sorting through a MACS, as recommended by the manufacturer. The lymphocytes were frozen and then thawed the day before the coculture with dendritic cells.

IV. Mixed Lymphocyte/Dendritic Cell Culture

Dendritic cells ($5 \times 10^5$/ml) were incubated at 37° C., 5% $CO_2$, for 18–20 h in complete medium supplemented with IL-4 (100 U/ml), GM-CSF (100 ng/ml) and TNF-α (1 ng/ml) in the presence of approximately 20 μg of the MAGE-A1® protein from batch no. 2. Cells were washed and added at $10^4$ per round-bottomed microwell to $10^5$ autologous CD4$^+$ lymphocytes in 200 μl IMDM medium supplemented with AAG and 10% human serum (hereafter referred to as complete IMDM medium) in the presence of IL-6 (1,000 U/ml) and IL-12 (10 ng/ml) (FIG. 1). The CD4$^+$ lymphocytes were restimulated on days 7 and 14 with autologous dendritic cells freshly loaded with MAGE-A1® protein from batch no. 2, and were grown in complete Iscove's medium supplemented with IL-2 (10 U/ml) and IL-7 (5 ng/ml). The fourth week, the stimulation was performed with an equivalent amount of dialysed MAGE-A1® protein from batch no. 1.

The microcultures containing proliferating CD4$^+$ T cells were assessed on day 35 for their capacity to produce IFN-γ when stimulated with autologous EBV-B cells loaded with protein MAGE-A1 ®. The reason another protein was used was to avoid taking into account the CD4$^+$ T cells reacting against contaminants contained in the protein used for loading the dendritic stimulator cells. Autologous EBV-B cells were incubated for 18–20 h in the presence of 20 μg/ml of protein MAGE-A1® or ovalbumin (OVA) (Sigma) as a negative control. Protein-pulsed EBV-B cells were washed and distributed at ~20,000 cells per round-bottomed microwell together with ~3,000 CD4$^+$ T lymphocytes in 150 μl of complete IMDM medium supplemented with IL-2 (25 U/ml). After 20 h, the supernatant was collected and its IFN-γ content was measured by ELISA using reagents from Medgenix Diagnostics-Biosource (Fleurus, Belgium).

V. A CD4$^+$ T Cell Clone Directed Against a MAGE-A1 Antigen

Figure 2:
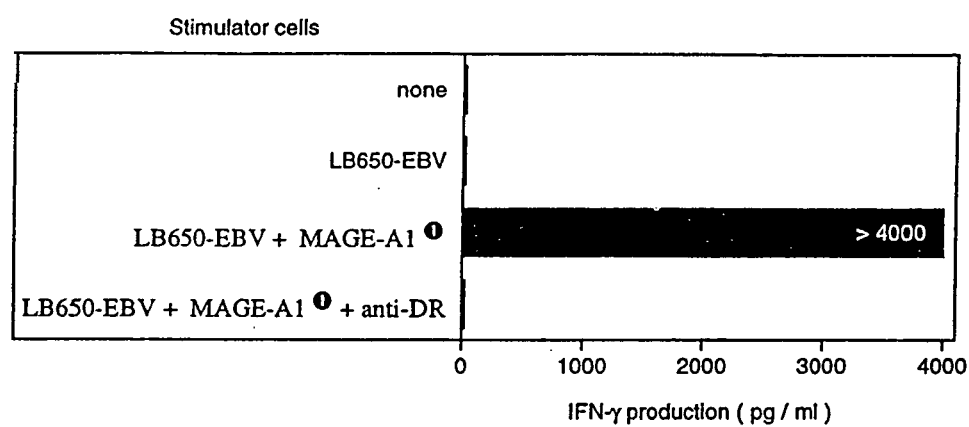
FIG. 2 shows that clone 14 recognizes a MAGE-A1 epitope presented by HLA-DR. LB650-EBV-B cells were indcubated in the presence of 10 µg/ml of the recombinant MAGE-A1® protein produced in *E. coli*. Clone 14 (~3000 cells) was incubated with ~10,000 EBV-MAGE-A 1 in round bottomed microwells for 18 hrs without monoclonal antibody [mAb] (medium) or in the presence of either mAb W6/32 (anti-HLA-A, B, C) or 2B6 (anti-HLA-DR). IFN-γ production in the supernatant was measured by ELISA.

Microculture G3, which produced a high level of IFN-γ after stimulation with protein MAGE-A1®, was cloned by limiting dilution using autologous EBV-B cells loaded with protein MAGE-A1® as stimulator cells ($5 \times 10^3$ to $10 \times 10^4$ cells per microwell). These stimulator cells were used for the cloning step because of the limited supply of autologous dendritic cells. Allogeneic LG2-EBV-B cells ($5 \times 10^3$ to $10 \times 10^4$ cells per microwell) were added as feeder cells. CD4$^+$ T cell clones were restimulated once a week and grown in complete IMDM medium supplemented with IL-2 (50 U/ml) and 0.5 μg/ml purified PHA (HA 16, Murex Diagnostics, Dartford, UK). Established CD4$^+$ T cell clones were supplemented with fresh culture medium once a week and passaged with feeder cells ($1.5 \times 10^6$ allogeneic PBL plus $5 \times 10^5$ LG2 EBV-B cells per well in a 24 wells plate) at 1–2 weeks intervals. CD4$^+$ clone LB650-CTL 488/G3.14 (referred to hereafter as clone 14) was obtained. It recognized autologous EBV-B cells loaded with protein MAGE-A1® (FIG. 2).

The recognition by clone 14 of cells loaded with protein MAGE-A1 was abolished by an anti-HLA-DR antibody. MAGE-A1®-pulsed EBV-B cells were cocultured for 24 hrs at 37° C. under 8% $CO_2$ with clone 14 in the continuous presence of preservative-free monoclonal antibodies used at a 1/20 dilution. Monoclonal antibody 2B6 (against HLA-DR) abolished the recognition whereas the recognition was unchanged in the presence of monoclonal antibody W6/32 (against HLA-A, B, C).

VI. CD4 Clone 14 Recognizes MAGE-A1 Peptide EYVIKVSARVRF (SEQ ID NO:7) on HLA-DRB1*15

In order to identify the MAGE-A1 peptide recognized by CD4 clone 14, 16 amino acid peptides corresponding to overlapping parts of the MAGE-A1 protein sequence (SEQ ID NO: 2) were loaded on the autologous EBV-B cells and tested for recognition. Peptides were synthesized on solid phase using F-moc for transient $NH_2$-terminal protection and were characterized using mass spectrometry. All peptides were >80% pure, as indicated by analytical HPLC. Lyophilized peptides were first dissolved at 2 mg/ml in DMSO and then diluted in Iscove's medium to be used at a concentration of 5 μg/ml. EBV-B cells were incubated for 2 h at 37° C. in the presence of the different peptides, the indicated concentrations representing their concentrations during the incubation step. They were distributed at 10,000 cells per round-bottomed microwell together with ~2,500 CD4$^+$ T lymphocytes in 100 μl of complete IMDM medium supplemented with IL-2 (25 U/ml). After 18–20 hrs, supernatants were harvested and assessed for IFN-γ secretion. IFN-γ production was measured using an ELISA test (20–4000 pg/ml) developed in the laboratory with reagents from Medgenix Diagnostics-Biosource (Fleurus, Belgium).

Figure 3:
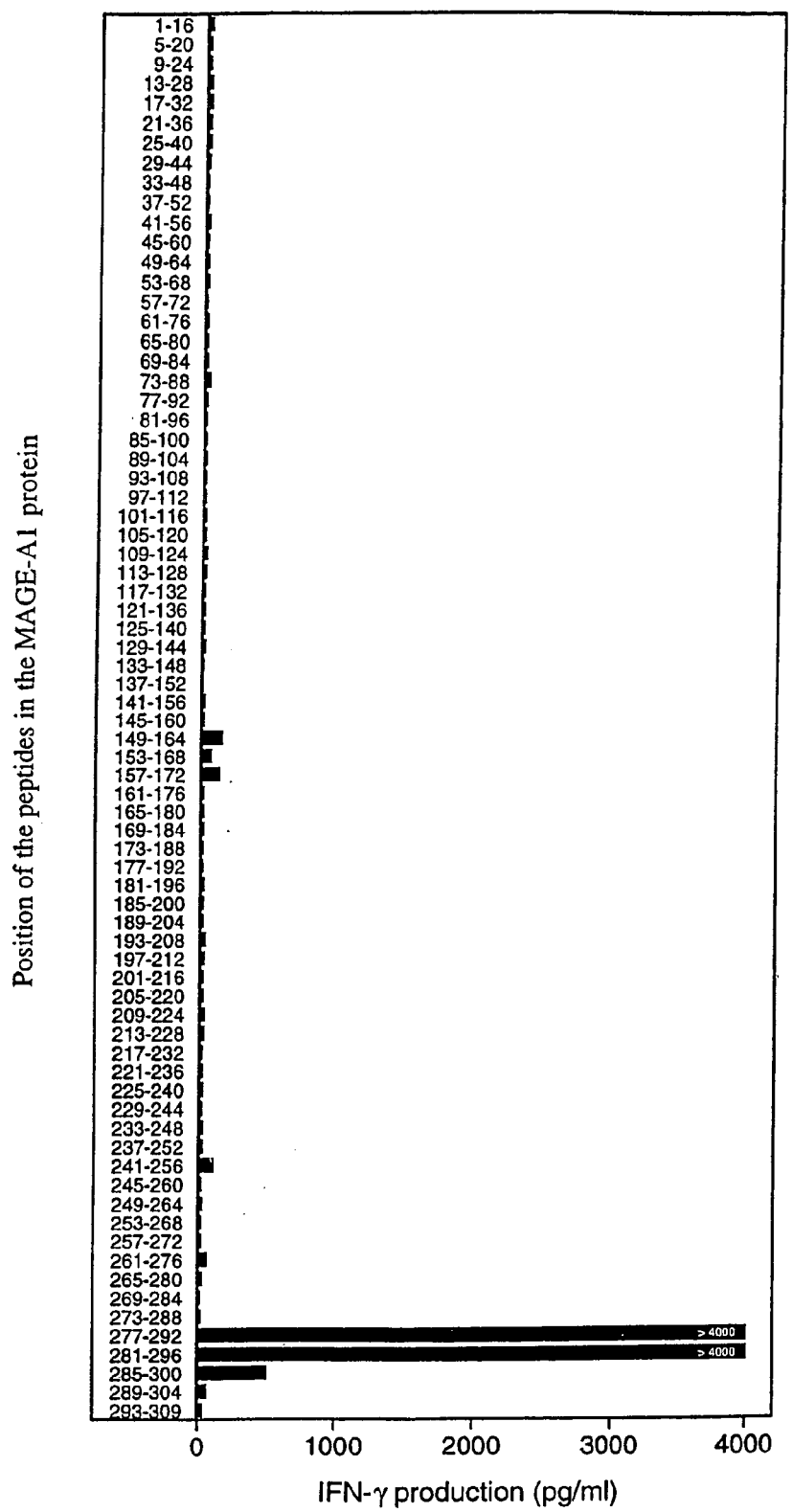
FIG. 3 depicts screening of MAGE-A1 peptides for recognition by clone 14. Autologous EBV-B cells (~10,000 per microwell) were pulsed with 5 µg/ml of peptides for 2 hrs before adding ~3000 cells of clone 14. After 18 hrs of coculture, IFN-γ production in the supernatant was measured by ELISA.
Figure 4:
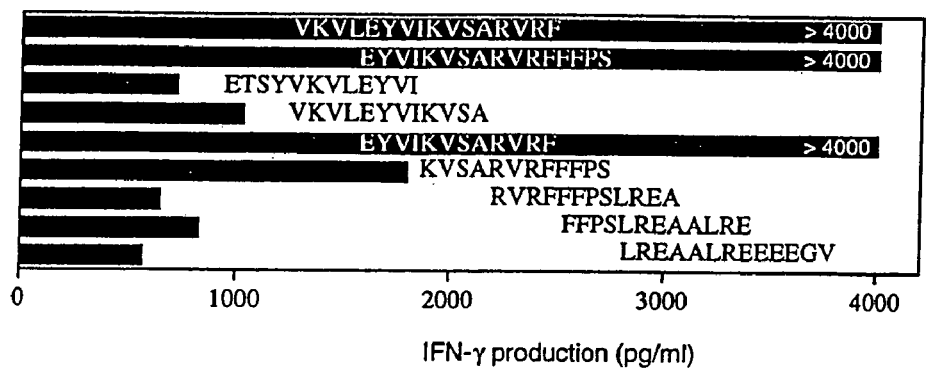
FIG. 4 shows that clone 14 recognizes peptide EYVIKVSARVRF (SEQ ID NO:7) and other MAGE-A1 peptides.
Figure 4:
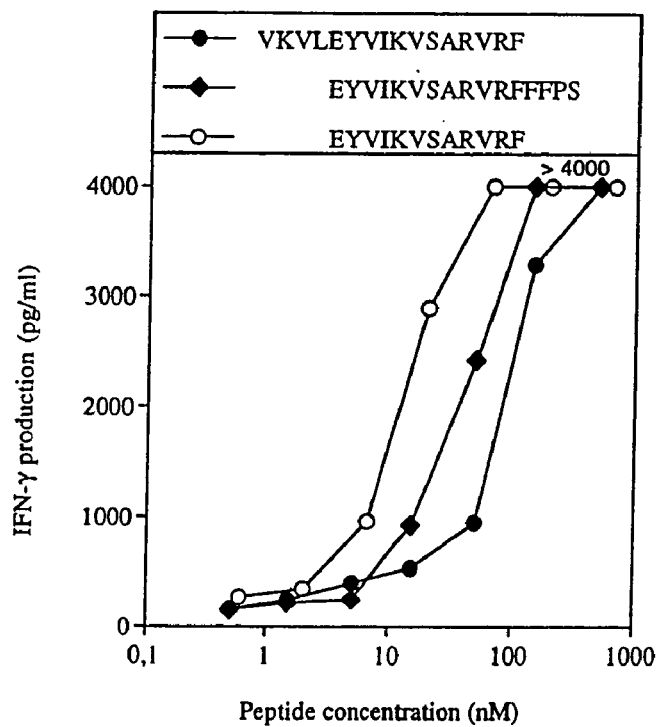

Two peptides scored positive, namely VKVLEYVIKVSARVRF (aa 277–292; SEQ ID NO:3) and EYVIKVSARVRFFFPS (aa 281–296; SEQ ID NO:4) (FIG. 3). They overlapped by 12 amino acids. Unlike the peptides presented by class I molecules, those presented by class II usually vary in length and tolerate extensions at both the amino and carboxy termini, because they are not fixed by their ends in the class II molecule groove. It is difficult, therefore, to define the length of those peptides precisely. Another set of 12 amino acid peptides was tested whose sequences were included in those of the two positive 16 amino acid peptides (FIG. 4). Peptide EYVIKVSARVRF (aa 281–292; SEQ ID NO: 7) is well recognized by clone 14 (FIG. 4). Half maximum value of stimulation was obtained by incubating the stimulator cells with ~10 nM of this peptide. This compares favorably with the results obtained with other MAGE epitopes recognized on HLA class II molecules by CD4$^+$ T cells. For example, ~10 nM of a MAGE-A3 peptide was needed to induce an half maximum production of IFN-γ of an anti-MAGE-A3 CD4$^+$ clone.

Patient LB650 was serologically typed DRB1*0701, DRB1*15 and DRB4*01 and DRB5*0101. To identify the presenting HLA-DR molecule, additional EBV-B cell lines expressing DRB1*0701, DRB1*15 and DRB4*01 or DRB5*0101 were tested. All and only those expressing DRB1*15 were able to present the MAGE-A1$_{281-292}$ peptide to clone 14 (Table 2).

TABLE 2

Clone 14 recognizes MAGE-A1 peptide EYVIKVSARVRF (SEQ. ID NO.: 7) on HLA–DRB1 * 15.

| EBV-B cell I | Serological specificity | IFN-γ production (pg/ml) by clone 14 stimulated with peptide EYVIKVSARVRF (SEQ. ID NO.: 7) |
|---|---|---|
| DR15 positive | | |
| LB 650 | DR7+ DR53+ DR51+ | >4000 |
| LB 1622 | DR13+ DR52+ DR51+ | 2940 |
| LB 1856 | DR0+ | 3240 |
| LB 1870 | DR7+ DR53+ | 1946 |
| DR15 negative | | |
| LB 1867 | DR7+ DR8+ DR11+ DR52+ | 71 |
| LB 1532 | DR8+ DR17+ DR52+ | 72 |
| LB 1555 | DR4+ DR17+ DR52+ | 63 |
| LB 2009 | DR7+ DR17+ DR52+ DR53+ | 83 |
| LB 1158 | DR1+ DR13+ DR52+ | 77 |
| LB 1860 | DR7+ DR14+ DR53+ | 74 |
| LB 1859 | DR4+ DR13+ | 76 |
| LB 1858 | DR7+ DR11+ | 61 |
| LB 1868 | DR3+ DR12+ DR52+ | 82 |
| LB 1863 | DR7+ DR52+ DR53+ | 73 |
| LB 1801 | DR12+ DR13+ DR52+ DR53+ | 78 |
| LB 1118 | DR13+ DR17+ DR53+ | 83 |
| LB 1857 | DR3+ DR14+ DR52+ | 57 |
| LB 1981 | DR4+ DR17+ DR52+ | 55 |

Autologous LB650 EBV-B cells or allogeneic EBV-B cells were pulsed with peptide EYVIKVSARVRF (SEQ ID NO: 7) at 1 µM for 2 hrs and washed. 10,000 peptide-pulsed EBV were incubated in round-bottomed microwells with 3,000 cells of CD4 Clone 14 for 18 hrs. IFN-γ production in the supernatant was measured by ELISA.

Example 2

Recognition of Other MAGE Proteins by Clone 14

Peptide sequences homologous to the MAGE-A1 HLA binding peptides described herein are found in other cancer antigens including MAGE-A4. For example, MAGE-A4 peptides were synthesized: YVKVLEHVVRVNARVR (SEQ ID NO:13) and LEHVVRVNARVRIAYP (SEQ ID NO:14). To determine if the CD4$^+$ T cell clones recognize these MAGE-A4 peptides, the peptides are used to load antigen presenting cells (such as EBV-B cells) to test for recognition by clone 14 according to the assays described above. To determine if the CD4$^+$ T cell clones recognize additional cancer associated antigens, the recombinant proteins (e.g. MAGE proteins) or other synthetic peptides corresponding to the homologous region in these proteins, are used as described above. Homologous peptides which are recognized by clone 14 may be regarded as functional variants of the MAGE-A1 peptides described herein.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated HLA DRB1*15-binding peptide consisting of
   the amino acid sequence set forth as SEQ ID NO:7 with 0–10 amino acids added to either or both ends of the amino acid sequence set forth as SEQ ID NO:7, and
   an endosomal targeting signal comprising an endosomal targeting portion of human invariant chain Ii or LAMP-1.

2. The isolated HLA DRB1*15-binding peptide of claim 1 wherein the amino acid sequence is selected from the group consisting of SEQ ID NO:3, SEQ ID NO:4, and SEQ ID NO:7.

3. The isolated HLA DRB1*15-binding peptide of claim 1 wherein the isolated peptide is non-hydrolyzable.

4. An isolated non-hydrolyzable HLA DRB1*15-binding peptide is selected from the group consisting of peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene)amino peptide bond, peptides comprising a -psi[CH$_2$CH(OH)]-hydroxyethylene peptide bond, peptides comprising a -psi[CH$_2$O]-peptide bond, and peptides comprising a -psi[CH2S]-thiomethylene peptide bond;
   wherein the amino acid sequence of the peptide consists of the amino acid sequence set forth as SEQ ID NO:7 with 0–10 amino acids added to either or both ends of the amino acid sequence set forth as SEQ ID NO:7, and
   an endosomal targeting signal comprising an endosomal targeting portion of human invariant chain Ii or LAMP-1.

5. A composition comprising
   an isolated MAGE-A1 HLA class I-binding peptide, and
   the isolated MAGE-A1 HLA DRB1*15-binding peptide of claim 1,
   wherein the HLA class I-binding peptide and the MAGE-A1 HLA DRB1*15-binding peptide are separate isolated peptides.

6. The composition of claim 5 wherein the amino acid sequence selected from the group consisting of SEQ ID NO:3, SEQ ID NO:4, and SEQ ID NO:7.

7. The composition of claim 5 wherein the isolated peptide is non-hydrolyzable.

8. A composition comprising
   an isolated MAGE-A1 HLA class I-binding peptide, and
   the isolated non-hydrolyzable MAGE-A1 HLA DRB1*15-binding peptide of claim 4,
   wherein the HLA class I-binding peptide and the non-hydrolyzable MAGE-A1 HLA DRB1*15-binding peptide are separate isolated peptides.

* * * * *

SEQUENCE LISTING

<160> NUMBER OF SEQ ID NOS: 73

<210> SEQ ID NO 1
<211> LENGTH: 1624
<212> TYPE: DNA
<213> ORGANISM: Homo sapiens

<400> SEQUENCE: 1

```
gttttcaggg gacaggccaa cccagaggac aggattccct ggaggccaca gaggagcacc      60
aaggagaaga tctgcctgtg ggtcttcatt gcccagctcc tgcccacact cctgcctgct     120
gccctgacga gagtcatcat gtctcttgag cagaggagtc tgcactgcaa gcctgaggaa     180
gcccttgagg cccaacaaga ggccctgggc ctggtgtgtg tgcaggctgc cacctcctcc     240
tcctctcctc tggtcctggg caccctggag gaggtgccca ctgctgggtc aacagatcct     300
ccccagagtc ctcagggagc ctccgccttt cccactacca tcaacttcac tcgacagagg     360
caacccagtg agggttccag cagccgtgaa gaggaggggc caagcacctc ttgtatcctg     420
gagtccttgt tccgagcagt aatcactaag aaggtggctg atttggttgg ttttctgctc     480
ctcaaatatc gagccaggga gccagtcaca aaggcagaaa tgctggagag tgtcatcaaa     540
aattacaagc actgttttcc tgagatcttc ggcaaagcct ctgagtcctt gcagctggtc     600
```

-continued

```
tttggcattg acgtgaagga agcagacccc accggccact cctatgtcct tgtcacctgc    660
ctaggtctct cctatgatgg cctgctgggt gataatcaga tcatgcccaa gacaggcttc    720
ctgataattg tcctggtcat gattgcaatg gagggcggcc atgctcctga ggaggaaatc    780
tgggaggagc tgagtgtgat ggaggtgtat gatgggaggg agcacagtgc ctatggggag    840
cccaggaagc tgctcaccca agatttggtg caggaaaagt acctggagta ccggcaggtg    900
ccggacagtg atcccgcacg ctatgagttc ctgtgggtc caagggccct cgctgaaacc    960
agctatgtga agtccttga gtatgtgatc aaggtcagtg caagagttcg cttttcttc     1020 ccatccctgc gtgaagcagc tttgagagag gaggaagagg gagtctgagc atgagttgca   1080
gccaaggcca gtgggagggg gactgggcca gtgcaccttc cagggccgcg tccagcagct   1140
tcccctgcct cgtgtgacat gaggcccatt cttcactctg aagagagcgg tcagtgttct   1200
cagtagtagg tttctgttct attgggtgac ttggagattt atctttgttc tcttttggaa   1260
ttgttcaaat gttttttttt aagggatggt tgaatgaact tcagcatcca agtttatgaa   1320
tgacagcagt cacacagttc tgtgtatata gtttaagggt aagagtcttg tgttttattc   1380
agattgggaa atccattcta ttttgtgaat tgggataata acagcagtgg aataagtact   1440
tagaaatgtg aaaaatgagc agtaaaatag atgagataaa gaactaaaga aattaagaga   1500
tagtcaattc ttgccttata cctcagtcta ttctgtaaaa tttttaaaga tatatgcata   1560
cctggatttc cttggcttct ttgagaatgt aagagaaatt aaatctgaat aaagaattct   1620
tcct                                                                1624
```

<210> SEQ ID NO 2
<211> LENGTH: 309
<212> TYPE: PRT
<213> ORGANISM: Homo sapiens

<400> SEQUENCE: 2

```
Met Ser Leu Glu Gln Arg Ser Leu His Cys Lys Pro Glu Glu Ala Leu
 1               5                  10                  15

Glu Ala Gln Gln Glu Ala Leu Gly Leu Val Cys Val Gln Ala Ala Thr
            20                  25                  30

Ser Ser Ser Ser Pro Leu Val Leu Gly Thr Leu Glu Glu Val Pro Thr
        35                  40                  45

Ala Gly Ser Thr Asp Pro Pro Gln Ser Pro Gln Gly Ala Ser Ala Phe
    50                  55                  60

Pro Thr Thr Ile Asn Phe Thr Arg Gln Arg Gln Pro Ser Glu Gly Ser
65                  70                  75                  80

Ser Ser Arg Glu Glu Gly Pro Ser Thr Ser Cys Ile Leu Glu Ser
            85                  90                  95

Leu Phe Arg Ala Val Ile Thr Lys Lys Val Ala Asp Leu Val Gly Phe
            100                 105                 110

Leu Leu Leu Lys Tyr Arg Ala Arg Glu Pro Val Thr Lys Ala Glu Met
        115                 120                 125

Leu Glu Ser Val Ile Lys Asn Tyr Lys His Cys Phe Pro Glu Ile Phe
    130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
```

```
              180                 185                 190
Gly Phe Leu Ile Ile Val Leu Val Met Ile Ala Met Glu Gly Gly His
            195                 200                 205
Ala Pro Glu Glu Ile Trp Glu Leu Ser Val Met Glu Val Tyr
    210                 215                 220
Asp Gly Arg Glu His Ser Ala Tyr Gly Glu Pro Arg Lys Leu Leu Thr
225                 230                 235                 240
Gln Asp Leu Val Gln Glu Lys Tyr Leu Glu Tyr Arg Gln Val Pro Asp
                245                 250                 255
Ser Asp Pro Ala Arg Tyr Glu Phe Leu Trp Gly Pro Arg Ala Leu Ala
            260                 265                 270
Glu Thr Ser Tyr Val Lys Val Leu Glu Tyr Val Ile Lys Val Ser Ala
        275                 280                 285
Arg Val Arg Phe Phe Phe Pro Ser Leu Arg Glu Ala Ala Leu Arg Glu
    290                 295                 300
Glu Glu Glu Gly Val
305

<210> SEQ ID NO 3
<211> LENGTH: 16
<212> TYPE: PRT
<213> ORGANISM: Homo sapiens

<400> SEQUENCE: 3

Val Lys Val Leu Glu Tyr Val Ile Lys Val Ser Ala Arg Val Arg Phe
1               5                   10                  15

<210> SEQ ID NO 4
<211> LENGTH: 16
<212> TYPE: PRT
<213> ORGANISM: Homo sapiens

<400> SEQUENCE: 4

Glu Tyr Val Ile Lys Val Ser Ala Arg Val Arg Phe Phe Phe Pro Ser
1               5                   10                  15

<210> SEQ ID NO 5
<211> LENGTH: 12
<212> TYPE: PRT
<213> ORGANISM: Homo sapiens

<400> SEQUENCE: 5

Glu Thr Ser Tyr Val Lys Val Leu Glu Tyr Val Ile
1               5                   10

<210> SEQ ID NO 6
<211> LENGTH: 12
<212> TYPE: PRT
<213> ORGANISM: Homo sapiens

<400> SEQUENCE: 6

Val Lys Val Leu Glu Tyr Val Ile Lys Val Ser Ala
1               5                   10

<210> SEQ ID NO 7
<211> LENGTH: 12
<212> TYPE: PRT
<213> ORGANISM: Homo sapiens

<400> SEQUENCE: 7

Glu Tyr Val Ile Lys Val Ser Ala Arg Val Arg Phe
```

-continued

<210> SEQ ID NO 8
<211> LENGTH: 12
<212> TYPE: PRT
<213> ORGANISM: Homo sapiens

<400> SEQUENCE: 8

Lys Val Ser Ala Arg Val Arg Phe Phe Phe Pro Ser
1               5                   10

<210> SEQ ID NO 9
<211> LENGTH: 12
<212> TYPE: PRT
<213> ORGANISM: Homo sapiens

<400> SEQUENCE: 9

Arg Val Arg Phe Phe Phe Pro Ser Leu Arg Glu Ala
1               5                   10

<210> SEQ ID NO 10
<211> LENGTH: 12
<212> TYPE: PRT
<213> ORGANISM: Homo sapiens

<400> SEQUENCE: 10

Phe Phe Pro Ser Leu Arg Glu Ala Ala Leu Arg Glu
1               5                   10

<210> SEQ ID NO 11
<211> LENGTH: 13
<212> TYPE: PRT
<213> ORGANISM: Homo sapiens

<400> SEQUENCE: 11

Leu Arg Glu Ala Ala Leu Arg Glu Glu Glu Gly Val
1               5                   10

<210> SEQ ID NO 12
<211> LENGTH: 36
<212> TYPE: DNA
<213> ORGANISM: Homo sapiens

<400> SEQUENCE: 12
gagtatgtga tcaaggtcag tgcaagagtt cgcttt                                 36

<210> SEQ ID NO 13
<211> LENGTH: 16
<212> TYPE: PRT
<213> ORGANISM: Homo sapiens

<400> SEQUENCE: 13

Tyr Val Lys Val Leu Glu His Val Val Arg Val Asn Ala Arg Val Arg
1               5                   10                  15

<210> SEQ ID NO 14
<211> LENGTH: 16
<212> TYPE: PRT
<213> ORGANISM: Homo sapiens

<400> SEQUENCE: 14

Leu Glu His Val Val Arg Val Asn Ala Arg Val Arg Ile Ala Tyr Pro
1               5                   10                  15

```
<210> SEQ ID NO 15
<211> LENGTH: 9
<212> TYPE: PRT
<213> ORGANISM: Homo sapiens

<400> SEQUENCE: 15

Glu Ala Asp Pro Thr Gly His Ser Tyr
 1               5

<210> SEQ ID NO 16
<211> LENGTH: 9
<212> TYPE: PRT
<213> ORGANISM: Homo sapiens

<400> SEQUENCE: 16

Ser Leu Phe Arg Ala Val Ile Thr Lys
 1               5

<210> SEQ ID NO 17
<211> LENGTH: 9
<212> TYPE: PRT
<213> ORGANISM: Homo sapiens

<400> SEQUENCE: 17

Asn Tyr Lys His Cys Phe Pro Glu Ile
 1               5

<210> SEQ ID NO 18
<211> LENGTH: 10
<212> TYPE: PRT
<213> ORGANISM: Homo sapiens

<400> SEQUENCE: 18

Glu Val Tyr Asp Gly Arg Glu His Ser Ala
 1               5                  10

<210> SEQ ID NO 19
<211> LENGTH: 10
<212> TYPE: PRT
<213> ORGANISM: Homo sapiens

<400> SEQUENCE: 19

Arg Glu Pro Val Thr Lys Ala Glu Met Leu
 1               5                  10

<210> SEQ ID NO 20
<211> LENGTH: 9
<212> TYPE: PRT
<213> ORGANISM: Homo sapiens

<400> SEQUENCE: 20

Asp Pro Ala Arg Tyr Glu Phe Leu Trp
 1               5

<210> SEQ ID NO 21
<211> LENGTH: 9
<212> TYPE: PRT
<213> ORGANISM: Homo sapiens

<400> SEQUENCE: 21

Ser Ala Phe Pro Thr Thr Ile Asn Phe
 1               5

<210> SEQ ID NO 22
<211> LENGTH: 9
```

```
<212> TYPE: PRT
<213> ORGANISM: Homo sapiens

<400> SEQUENCE: 22

Ser Ala Tyr Gly Glu Pro Arg Lys Leu
1               5

<210> SEQ ID NO 23
<211> LENGTH: 14
<212> TYPE: PRT
<213> ORGANISM: Homo sapiens

<400> SEQUENCE: 23

Leu Leu Lys Tyr Arg Ala Arg Glu Pro Val Thr Lys Ala Glu
1               5                   10

<210> SEQ ID NO 24
<211> LENGTH: 10
<212> TYPE: PRT
<213> ORGANISM: Homo sapiens

<400> SEQUENCE: 24

Tyr Leu Gln Leu Val Phe Gly Ile Glu Val
1               5                   10

<210> SEQ ID NO 25
<211> LENGTH: 9
<212> TYPE: PRT
<213> ORGANISM: Homo sapiens

<400> SEQUENCE: 25

Glu Val Asp Pro Ile Gly His Leu Tyr
1               5

<210> SEQ ID NO 26
<211> LENGTH: 9
<212> TYPE: PRT
<213> ORGANISM: Homo sapiens

<400> SEQUENCE: 26

Phe Leu Trp Gly Pro Arg Ala Leu Val
1               5

<210> SEQ ID NO 27
<211> LENGTH: 9
<212> TYPE: PRT
<213> ORGANISM: Homo sapiens

<400> SEQUENCE: 27

Lys Val Ala Glu Leu Val His Phe Leu
1               5

<210> SEQ ID NO 28
<211> LENGTH: 9
<212> TYPE: PRT
<213> ORGANISM: Homo sapiens

<400> SEQUENCE: 28

Ile Met Pro Lys Ala Gly Leu Leu Ile
1               5

<210> SEQ ID NO 29
<211> LENGTH: 9
<212> TYPE: PRT
<213> ORGANISM: Homo sapiens
```

```
<400> SEQUENCE: 29

Thr Phe Pro Asp Leu Glu Ser Glu Phe
1               5

<210> SEQ ID NO 30
<211> LENGTH: 10
<212> TYPE: PRT
<213> ORGANISM: Homo sapiens

<400> SEQUENCE: 30

Met Glu Val Asp Pro Ile Gly His Leu Tyr
1               5                   10

<210> SEQ ID NO 31
<211> LENGTH: 14
<212> TYPE: PRT
<213> ORGANISM: Homo sapiens

<400> SEQUENCE: 31

Ala Glu Leu Val His Phe Leu Leu Leu Lys Tyr Arg Ala Arg
1               5                   10

<210> SEQ ID NO 32
<211> LENGTH: 15
<212> TYPE: PRT
<213> ORGANISM: Homo sapiens

<400> SEQUENCE: 32

Thr Ser Tyr Val Lys Val Leu His His Met Val Lys Ile Ser Gly
1               5                   10                  15

<210> SEQ ID NO 33
<211> LENGTH: 10
<212> TYPE: PRT
<213> ORGANISM: Homo sapiens

<400> SEQUENCE: 33

Gly Val Tyr Asp Gly Arg Glu His Thr Val
1               5                   10

<210> SEQ ID NO 34
<211> LENGTH: 9
<212> TYPE: PRT
<213> ORGANISM: Homo sapiens

<400> SEQUENCE: 34

Met Val Lys Ile Ser Gly Gly Pro Arg
1               5

<210> SEQ ID NO 35
<211> LENGTH: 12
<212> TYPE: PRT
<213> ORGANISM: Homo sapiens

<400> SEQUENCE: 35

Lys Ile Ser Gly Gly Pro Arg Ile Ser Tyr Pro Leu
1               5                   10

<210> SEQ ID NO 36
<211> LENGTH: 9
<212> TYPE: PRT
<213> ORGANISM: Homo sapiens

<400> SEQUENCE: 36
```

```
Gly Leu Tyr Asp Gly Met Glu His Leu
 1               5
```

<210> SEQ ID NO 37
<211> LENGTH: 9
<212> TYPE: PRT
<213> ORGANISM: Homo sapiens

<400> SEQUENCE: 37

```
Ala Ala Arg Ala Val Phe Leu Ala Leu
 1               5
```

<210> SEQ ID NO 38
<211> LENGTH: 8
<212> TYPE: PRT
<213> ORGANISM: Homo sapiens

<400> SEQUENCE: 38

```
Tyr Arg Pro Arg Pro Arg Arg Tyr
 1               5
```

<210> SEQ ID NO 39
<211> LENGTH: 9
<212> TYPE: PRT
<213> ORGANISM: Homo sapiens

<400> SEQUENCE: 39

```
Tyr Tyr Trp Pro Arg Pro Arg Arg Tyr
 1               5
```

<210> SEQ ID NO 40
<211> LENGTH: 11
<212> TYPE: PRT
<213> ORGANISM: Homo sapiens

<400> SEQUENCE: 40

```
Gln Leu Ser Leu Leu Met Trp Ile Thr Gln Cys
 1               5                  10
```

<210> SEQ ID NO 41
<211> LENGTH: 11
<212> TYPE: PRT
<213> ORGANISM: Homo sapiens

<400> SEQUENCE: 41

```
Ser Leu Leu Met Trp Ile Thr Gln Cys Phe Leu
 1               5                  10
```

<210> SEQ ID NO 42
<211> LENGTH: 9
<212> TYPE: PRT
<213> ORGANISM: Homo sapiens

<400> SEQUENCE: 42

```
Ser Leu Leu Met Trp Ile Thr Gln Cys
 1               5
```

<210> SEQ ID NO 43
<211> LENGTH: 9
<212> TYPE: PRT
<213> ORGANISM: Homo sapiens

<400> SEQUENCE: 43

Gln Leu Ser Leu Leu Met Trp Ile Thr

```
                1               5
```

<210> SEQ ID NO 44
<211> LENGTH: 10
<212> TYPE: PRT
<213> ORGANISM: Homo sapiens

<400> SEQUENCE: 44

```
Ala Ser Gly Pro Gly Gly Gly Ala Pro Arg
  1               5                  10
```

<210> SEQ ID NO 45
<211> LENGTH: 10
<212> TYPE: PRT
<213> ORGANISM: Homo sapiens

<400> SEQUENCE: 45

```
Leu Ala Ala Gln Glu Arg Arg Val Pro Arg
  1               5                  10
```

<210> SEQ ID NO 46
<211> LENGTH: 9
<212> TYPE: PRT
<213> ORGANISM: Homo sapiens

<400> SEQUENCE: 46

```
Val Leu Pro Asp Val Phe Ile Arg Cys
  1               5
```

<210> SEQ ID NO 47
<211> LENGTH: 10
<212> TYPE: PRT
<213> ORGANISM: Homo sapiens

<400> SEQUENCE: 47

```
Val Leu Pro Asp Val Phe Ile Arg Cys Val
  1               5                  10
```

<210> SEQ ID NO 48
<211> LENGTH: 10
<212> TYPE: PRT
<213> ORGANISM: Homo sapiens

<400> SEQUENCE: 48

```
Glu Val Ile Ser Cys Lys Leu Ile Lys Arg
  1               5                  10
```

<210> SEQ ID NO 49
<211> LENGTH: 10
<212> TYPE: PRT
<213> ORGANISM: Homo sapiens

<400> SEQUENCE: 49

```
Ser Pro Ser Ser Asn Arg Ile Arg Asn Thr
  1               5                  10
```

<210> SEQ ID NO 50
<211> LENGTH: 9
<212> TYPE: PRT
<213> ORGANISM: Homo sapiens

<400> SEQUENCE: 50

```
Glu Glu Lys Leu Ile Val Val Leu Phe
  1               5
```

```
<210> SEQ ID NO 51
<211> LENGTH: 9
<212> TYPE: PRT
<213> ORGANISM: Homo sapiens

<400> SEQUENCE: 51

Glu Glu Lys Leu Ser Val Val Leu Phe
1               5

<210> SEQ ID NO 52
<211> LENGTH: 10
<212> TYPE: PRT
<213> ORGANISM: Homo sapiens

<400> SEQUENCE: 52

Ala Cys Asp Pro His Ser Gly His Phe Val
1               5                   10

<210> SEQ ID NO 53
<211> LENGTH: 10
<212> TYPE: PRT
<213> ORGANISM: Homo sapiens

<400> SEQUENCE: 53

Ala Arg Asp Pro His Ser Gly His Phe Val
1               5                   10

<210> SEQ ID NO 54
<211> LENGTH: 9
<212> TYPE: PRT
<213> ORGANISM: Homo sapiens

<400> SEQUENCE: 54

Ser Tyr Leu Asp Ser Gly Ile His Phe
1               5

<210> SEQ ID NO 55
<211> LENGTH: 9
<212> TYPE: PRT
<213> ORGANISM: Homo sapiens

<400> SEQUENCE: 55

Ser Tyr Leu Asp Ser Gly Ile His Ser
1               5

<210> SEQ ID NO 56
<211> LENGTH: 9
<212> TYPE: PRT
<213> ORGANISM: Homo sapiens

<400> SEQUENCE: 56

Met Leu Leu Ala Val Leu Tyr Cys Leu
1               5

<210> SEQ ID NO 57
<211> LENGTH: 9
<212> TYPE: PRT
<213> ORGANISM: Homo sapiens

<400> SEQUENCE: 57

Tyr Met Asn Gly Thr Met Ser Gln Val
1               5

<210> SEQ ID NO 58
```

-continued

```
<211> LENGTH: 9
<212> TYPE: PRT
<213> ORGANISM: Homo sapiens

<400> SEQUENCE: 58

Tyr Met Asp Gly Thr Met Ser Gln Val
1               5

<210> SEQ ID NO 59
<211> LENGTH: 9
<212> TYPE: PRT
<213> ORGANISM: Homo sapiens

<400> SEQUENCE: 59

Ala Phe Leu Pro Trp His Arg Leu Phe
1               5

<210> SEQ ID NO 60
<211> LENGTH: 9
<212> TYPE: PRT
<213> ORGANISM: Homo sapiens

<400> SEQUENCE: 60

Ser Glu Ile Trp Arg Asp Ile Asp Phe
1               5

<210> SEQ ID NO 61
<211> LENGTH: 9
<212> TYPE: PRT
<213> ORGANISM: Homo sapiens

<400> SEQUENCE: 61

Tyr Glu Ile Trp Arg Asp Ile Asp Phe
1               5

<210> SEQ ID NO 62
<211> LENGTH: 15
<212> TYPE: PRT
<213> ORGANISM: Homo sapiens

<400> SEQUENCE: 62

Gln Asn Ile Leu Leu Ser Asn Ala Pro Leu Gly Pro Gln Phe Pro
1               5                   10                  15

<210> SEQ ID NO 63
<211> LENGTH: 15
<212> TYPE: PRT
<213> ORGANISM: Homo sapiens

<400> SEQUENCE: 63

Asp Tyr Ser Tyr Leu Gln Asp Ser Asp Pro Asp Ser Phe Gln Asp
1               5                   10                  15

<210> SEQ ID NO 64
<211> LENGTH: 9
<212> TYPE: PRT
<213> ORGANISM: Homo sapiens

<400> SEQUENCE: 64

Ala Ala Gly Ile Gly Ile Leu Thr Val
1               5

<210> SEQ ID NO 65
<211> LENGTH: 10
<212> TYPE: PRT
```

<213> ORGANISM: Homo sapiens

<400> SEQUENCE: 65

Glu Ala Ala Gly Ile Gly Ile Leu Thr Val
1               5                   10

<210> SEQ ID NO 66
<211> LENGTH: 9
<212> TYPE: PRT
<213> ORGANISM: Homo sapiens

<400> SEQUENCE: 66

Ile Leu Thr Val Ile Leu Gly Val Leu
1               5

<210> SEQ ID NO 67
<211> LENGTH: 9
<212> TYPE: PRT
<213> ORGANISM: Homo sapiens

<400> SEQUENCE: 67

Lys Thr Trp Gly Gln Tyr Trp Gln Val
1               5

<210> SEQ ID NO 68
<211> LENGTH: 9
<212> TYPE: PRT
<213> ORGANISM: Homo sapiens

<400> SEQUENCE: 68

Ile Thr Asp Gln Val Pro Phe Ser Val
1               5

<210> SEQ ID NO 69
<211> LENGTH: 9
<212> TYPE: PRT
<213> ORGANISM: Homo sapiens

<400> SEQUENCE: 69

Tyr Leu Glu Pro Gly Pro Val Thr Ala
1               5

<210> SEQ ID NO 70
<211> LENGTH: 10
<212> TYPE: PRT
<213> ORGANISM: Homo sapiens

<400> SEQUENCE: 70

Leu Leu Asp Gly Thr Ala Thr Leu Arg Leu
1               5                   10

<210> SEQ ID NO 71
<211> LENGTH: 10
<212> TYPE: PRT
<213> ORGANISM: Homo sapiens

<400> SEQUENCE: 71

Val Leu Tyr Arg Tyr Gly Ser Phe Ser Val
1               5                   10

<210> SEQ ID NO 72
<211> LENGTH: 9
<212> TYPE: PRT
<213> ORGANISM: Homo sapiens

```
-continued

<400> SEQUENCE: 72

Leu Tyr Val Asp Ser Leu Phe Phe Leu
 1               5

<210> SEQ ID NO 73
<211> LENGTH: 7
<212> TYPE: PRT
<213> ORGANISM: Homo sapiens

<400> SEQUENCE: 73

His His His His His His His
 1               5
```